(12) United States Patent
Imamoto et al.

(10) Patent No.: US 7,084,623 B2
(45) Date of Patent: Aug. 1, 2006

(54) NON-DESTRUCTIVE INSPECTION DEVICE AND METHOD UTILIZING A MAGNETIC FIELD AND SENSOR COIL ARRAY

(75) Inventors: Kazunobu Imamoto, Osaka (JP); Takashi Kimura, Aichi (JP)

(73) Assignees: Daihatsu Motor Co., Ltd., Osaka (JP); Magnegraph Co., Ltd., Aichi (JP)

( * ) Notice: Subject to any disclaimer, the term of this patent is extended or adjusted under 35 U.S.C. 154(b) by 128 days.

(21) Appl. No.: 10/490,724

(22) PCT Filed: Sep. 24, 2002

(86) PCT No.: PCT/JP02/09799

§ 371 (c)(1),
(2), (4) Date: Jun. 23, 2004

(87) PCT Pub. No.: WO03/027660

PCT Pub. Date: Apr. 3, 2003

(65) Prior Publication Data

US 2004/0232909 A1    Nov. 25, 2004

(30) Foreign Application Priority Data

Sep. 25, 2001    (JP) ............................. 2001-292329

(51) Int. Cl.
*G01N 27/82* (2006.01)
(52) U.S. Cl. ...................................... 324/240; 324/225
(58) Field of Classification Search ................ 324/225, 324/234–243
See application file for complete search history.

(56) References Cited

U.S. PATENT DOCUMENTS

| 5,512,821 A | * | 4/1996 | Ando et al. .................. 324/225 |
| 6,150,809 A | * | 11/2000 | Tiernan et al. .............. 324/238 |
| 6,232,774 B1 | | 5/2001 | Kimura |

FOREIGN PATENT DOCUMENTS

| JP | 7-128294 | 5/1995 |
| JP | 2000-227419 | 8/2000 |
| JP | 2001-165911 | 6/2001 |

OTHER PUBLICATIONS

Kimura et al. "Nugget Profiler". *Inspection Engineering*, vol. 6, No. 6, pp. 50-54 (Jun. 1, 2001).

Imamoto et al. "The Measure for the Non-destructive Test of Spot-Welded Joints". *Society of Automotive Engineers of Japan, Inc.*, No. 90-01, pp. 1-4 (Oct. 23, 2001) and English abstract.

* cited by examiner

*Primary Examiner*—Jay M. Patidar
(74) *Attorney, Agent, or Firm*—Hamre, Schumann, Mueller & Larson, P.C.

(57) ABSTRACT

A non-destructive inspection device (X1) includes an exciting pole (10) having a magnetic flux exciting surface (11) for exciting a magnetic flux to form a magnetic field in an inspection target, a recovering pole (30) having a magnetic flux recovering surface (31) for recovering the magnetic flux excited from the magnetic flux exciting surface (11), and a coil array (50) having a plurality of loop coils though which the magnetic flux excited from the magnetic flux exciting surface (11) passes prior to reaching the inspection target, the coil array being offset toward the recovering pole (30) with respect to the magnetic flux exciting surface (11).

8 Claims, 19 Drawing Sheets

NON-DESTRUCTIVE INSPECTION DEVICE AND METHOD UTILIZING A MAGNETIC FIELD AND SENSOR COIL ARRAY

TECHNICAL FIELD

The present invention relates to a non-destructive inspection device and a non-destructive inspection method for obtaining information relating to internal structure such as the state of welding, hardness and internal defects, in a magnetic member such as a steel plate, in a non-destructive manner.

BACKGROUND ART

Spot welding is a known welding technology for welding together metal plates, which can be used in the manufacture of automobiles, domestic electrical products, and the like. In spot welding, firstly, as illustrated in FIG. 23, two superimposed metal plates 100a, 100b are sandwiched between a pair of electrodes 150a, 150b. In this state, pressure is applied locally to the metal plates 100a, 100b by means of the pair of electrodes 150a, 150b, and current is passed between the electrodes 150a, 150b. The current flows in a concentrated manner through the portion of the metal plates 100a, 100b sandwiched between the electrodes 150a, 150b, and therefore generates Joule heat. A portion of the metal plates 100a, 100b is melted by this Joule heat, whereupon, the passage of current is halted. When the molten portion of the metal plates 100a, 100b cools and solidifies, the metal plates 100a, 100b will be welded together.

FIG. 24 is a cross-sectional view of a spot welded section of two metal plates 100a, 100b which have been spot welded as described above. In the spot welded section, the outer surfaces of the metal plates 100a, 100b are dented due to the pressure applied by the electrodes 150a, 150b. This denting is called an "indentation" 101, and the length L1 thereof is called the "indentation diameter". A nugget section 102 and a pressure bonded section 103 are formed in the spot weld section. The nugget section 102 in a region where the metal plates 100a, 100b have become unified as a result of being melted due to the application of heat and pressure, and then solidifying. The length L2 of the nugget section 102 is called the "nugget diameter". This nugget diameter L2 greatly influences the welding strength achieved in the spot weld section. The greater the nugget diameter L2, the greater the weld strength of the spot weld section. The pressure bonded section 103 is a region which has received the effects of the applied heat and applied pressure and where the metal plates 100a, 100b have bonded together under pressure. Together, the nugget section 102 and the pressure bonded section 103 are known as the "joint section 104", and the length L3 of this joint section 104 is called the joint diameter. The original material 105 surrounding the joint section 104 is a region which does not contribute to the joint strength of the spot weld.

Generally, the nugget diameter L2 or the pressure bond diameter L3 in the spot weld section achieved by welding is appropriately 10 millimeters or less, which is relatively small. Therefore, in many cases, it is necessary to inspect the spot weld section in order to check that it has sufficient weld strength. Since the weld strength of the spot weld section is greatly influenced by the nugget diameter L2, then the nugget diameter L2 can be used effectively as a basis for judging whether or not the spot weld section has a suitable welded state.

Japanese Patent Laid-open No. Hei10-26609 discloses inspection technology, one object of which is to measure the nugget diameter L2 in a non-destructive manner, and to judge the suitability or unsuitability of the welded state of a spot weld section on the basis of these measurement results. According to this patent publication, an exciting coil is disposed in the vicinity of an inspection target, and a loop coil forming a sensor is disposed between the inspection target and the exciting coil. In this state, a static magnetic field is generated which passes through the inspection target and the sensor, by passing a DC current through the exciting coil. Thereupon, when the static magnetic field is shut off, the inductance of the loop coil (or a physical quantity that is directly proportional to the inductance thereof) is determined by tracing the course of the loss of the electrical field remaining in the inspection target. This inductance indicates the magnetic permeability of the nugget section 102 and pressure bonded section 103, or the like, constituting the spot welding section through which the residual magnetic field passes. When measurement of this kind is carried out in a plurality of positions with respect to the inspection target, then variation will occur in the plurality of inductances obtained. This variation in inductance reflects variations in the internal structure of the spot weld section. Therefore, the nugget diameter L2 can be estimated by detecting the variations in magnetic permeability, and hence the variations in inductance, caused by changes in the internal structure of the spot weld section, by means of non-destructive inspection technology.

FIG. 25 shows a conventional non-destructive inspection device X2 for executing a non-destructive inspection method as described above. The non-destructive inspection device X2 comprises an exciting pole 210, an exciting coil 220 wound about this pole, a recovering pole 230, a connecting section 240 connecting the exciting pole 210 and the recovering pole 230, and a coil array 250 disposed in the vicinity of the exciting pole 210.

The exciting pole 210 is an iron core for raising the magnetic flux intensity of the magnetic field induced when a current flows in the exciting coil 220, and it is formed integrally with the recovering pole 230, by means of the connecting section 240. The exciting pole 210 has a finely pointed end and has a magnetic flux exciting surface 211 formed on the front end thereof. The magnetic flux exciting surface 211 is a face disposed opposing the inspection target, via the coil array 250. The exciting coil 220 is connected to a drive circuit (not illustrated) which incorporates a DC power supply, a switch and a prescribed resistance. The recovering pole 230 has a recovering surface 231 on the front end thereof. The magnetic flux excited from the magnetic flux exciting surface 211 of the exciting pole 210 is recovered by the recovering surface 231.

The coil array 250 serves to detect magnetic changes in the vicinity of the inspection target and output same in the form of a voltage, and consists of a prescribed number of loop coils 251 disposed sequentially in a position opposing the magnetic flux exciting surface 211. The loop coils 251 are made from a conducting material, such as Cu, and are patterned onto a flexible substrate (not illustrated).

FIG. 26 includes a cross-sectional view along line XXVI—XXVI in FIG. 25, showing a state where the switch of the drive circuit has been switched on and the voltage output by the DC power supply is applied to the exciting coil 220, thereby causing a static magnetic field F3 to be applied to the spot weld section of a steel plate 110. The internal portion of the steel plate 110 that the magnetic flux passes through is magnetized in accordance with the static magnetic field F3. The non-destructive inspection device X2 is composed in such a manner that it traces the course of the disappearance of the residual magnetic field in the magnetized location, after the static magnetic field F3 has been shut off, by means of various sensor coils 251, whereby it is possible to measure the time constant in the transient change of each course of disappearance of the magnetic flux.

However, in a conventional non-destructive inspection device X2, the distance of separation L4 between the magnetic flux exciting surface 211 and the magnetic recovering surface 231 is approximately 3 mm, which is relatively long. If the distance of separation L4 between the magnetic flux exciting surface 211 and the magnetic recovering surface 231 L4 is long, then after the static magnetic field F3 has been shut off, the distance traveled by the residual magnetic field passing through the regions other than the nugget section 102 also becomes longer, accordingly. Therefore, noise is liable to be introduced into the course of disappearance of the residual magnetic field, and hence there are cases where adequate information relating to the nugget section 102 cannot be obtained, from the viewpoints of accuracy and the S/N ratio.

Moreover, in the conventional non-destructive inspection device X2, the respective sensor coils 251 constituting the coil array 250 are provided throughout the whole length of the magnetic flux exciting surface 211, in the width direction L5 thereof. In a composition of this kind, even after the static magnetic field F3 has been shut off, a component of the course of disappearance of the residual magnetic field corresponding to the magnetic field F3 that did not pass through the nugget section 102 will still be detected, which is undesirable from the standpoints of accuracy and S/N ratio.

Furthermore, the width L5 of the magnetic flux exciting surface 211 of the conventional non-destructive inspection device X2 is formed to a narrower width than the width L6 of the exciting pole 210, and the surface area from which the magnetic flux is excited is small. Therefore, when the static magnetic field F3 is applied, the magnetic flux does not pass readily through the nugget section 102, in other words, cases where the spot weld section cannot be magnetized satisfactorily will occur.

In this way, the conventional non-destructive inspection device X2 entails problems in the magnetization of the spot weld section when applying the static magnetic field F3, and the detection of the residual magnetic field after the static magnetic field F3 has been shut off. Therefore, for example, there have been cases where it has not been possible to obtain sufficiently reliable results for the measurement of the nugget diameter L2 in a spot weld section, or the like.

DISCLOSURE OF THE INVENTION

It is an object of the present invention to provide a non-destructive inspection device and a non-destructive inspection method whereby highly reliable inspection results can be obtained by means of non-destructive inspection for acquiring information relating to the internal structure of a magnetic member, such as the state of welding, hardness or internal defects thereof, or the like.

According to a first aspect of the present invention, a non-destructive inspection device is provided. This non-destructive inspection device comprises: an exciting pole including a magnetic flux exciting surface for exciting a magnetic flux to form a magnetic field in an inspection target; a recovering pole including a magnetic flux recovering surface for recovering the magnetic flux excited from the magnetic flux exciting surface; and a coil array including a plurality of loop coils though which the magnetic flux excited from the magnetic flux exciting surface passes prior to reaching the inspection target, the coil array being offset toward the recovering pole with respect to the magnetic flux exciting surface.

With the above arrangement, it is possible to obtain highly reliable inspection results from the non-destructive inspection of the suitability or unsuitability, or the like, of the welded state in a spot weld section. In using this device, when a magnetic flux is excited by the exciting pole, the magnetic flux that is excited from the magnetic flux exciting surface is divided into a component that heads toward the recovering pole, in other words, a component that passes through the nugget section of the spot weld section, and a component that heads in the opposite direction. Since the coil array is disposed in a position that is offset toward the recovering pole, with respect to the magnetic flux exciting surface, then the amount of magnetic flux heading in the opposite direction that passes through the coil array is reduced. Consequently, the coil array is able to trace the change in the magnetic flux at the recovering pole, in other words, the magnetic flux passing through the nugget section, in a satisfactory manner. Therefore, the S/N ratio is improved and highly reliable inspection results can be obtained.

Preferably, the coil array may be disposed within a region between the center of the magnetic flux exciting surface as viewed widthwise thereof and the edge portion of the magnetic flux exciting surface adjacent to the recovering pole. In this manner, it is possible to ensure the beneficial effects described above.

Preferably, the distance of separation between the magnetic flux exciting surface and the magnetic flux recovering surface may be in a range of 1.0–2.0 mm. In a conventional non-destructive inspection device, as described above, the distance of separation between the magnetic flux exciting surface and the magnetic flux recovering surface is approximately 3 mm, which is relatively large. By contrast, in the present composition, the distance of separation between the magnetic flux exciting surface and the magnetic flux recovering surface is 1.0 to 2.0 mm, and therefore the distance traveled by the magnetic flux is shortened appropriately. The shorter the distance traveled by the magnetic flux, the greater the tendency to form a stable magnetic field. Consequently, in the course of the disappearance of the residual magnetic field, noise is reduced in the detection made by means of the loop coils forming the sensors, and hence the S/N ratio can be improved.

Preferably, the magnetic flux exciting surface and the magnetic flux recovering surface may have congruent shapes. In this manner, it is possible to excite a stable magnetic flux, and therefore, detection results of high accuracy can be obtained.

Preferably, the magnetic flux exciting surface may have the same width as the trunk portion of the exciting pole, throughout the entirety of the surface. In a conventional non-destructive inspection device, as described above, the exciting pole has a pointed shape, and comprises a flat magnetic flux exciting surface on the front end thereof. In other words, the magnetic flux exciting surface is narrower than the trunk portion of the exciting pole. By contrast, in the present invention, the magnetic flux exciting surface is formed so as to have the same width as the exciting pole through the entire length thereof, and therefore, as large as possible a surface area is ensured for the magnetic flux exciting surface. Consequently, the magnetic flux can pass more readily through the nugget section of the spot weld section, for example.

Preferably, the loop coils of the coil array may form a plurality of coil rows, and each coil row is disposed extending in a direction perpendicular to the direction in which the exciting pole and recovering pole are separated from each other. By this arrangement, it is possible to measure the change in magnetic flux over a larger surface area, in the depth direction of the inspection target, and consequently, it is possible to obtain a greater number of detection results, and results of higher accuracy.

According to a second aspect of the present invention, there is provided a non-destructive inspection method carried out using a non-destructive inspection device comprising: an exciting pole including a magnetic flux exciting surface for exciting a magnetic flux to form a magnetic field in an inspection target; a recovering pole having a magnetic flux recovering surface for recovering the magnetic flux excited from the magnetic flux exciting surface; and a coil array including a plurality of loop coils though which the magnetic flux excited from the magnetic flux exciting surface passes prior to reaching the inspection target, the coil array being offset toward the recovering pole with respect to the magnetic flux exciting surface. This non-destructive inspection method comprises the following steps: a step of magnetizing the inspection target by applying a first static magnetic field to the inspection target; a step of shutting off the first static magnetic field and measuring the transient change in the differential magnetic flux density at a plurality of positions in a first residual magnetic field passing through the magnetized inspection target; a step of determining a first time constant by the main time constant of the transient change at the respective measurement positions; a step of magnetizing the inspection target by applying a second static magnetic field to the inspection target; a step of shutting off the second static magnetic field and measuring the transient change of the differential magnetic flux density at the respective measurement positions in a second residual magnetic field passing through the magnetized inspection target; a step of determining a second time constant by the main time constant of the transient change at the respective measurement positions; and an information acquisition step of obtaining information relating to the internal structure of the inspection target, on the basis of the differences between the distribution of the first time constant and the distribution of the second time constant, at the measurement positions. By adopting a non-destructive inspection method of this kind based on results of the two series of inspection, it is possible to make inferences of a highly reliable nature regarding the internal structure, and the like, of the inspection target.

Preferably, the inspection target may be a spot weld section in a joined member formed by spot welding of two metal plates. In the information acquisition step, information relating to the shape of the nugget section contained in the spot weld section may be obtained.

BEST MODE FOR CARRYING OUT THE INVENTION

The present invention relates to a non-destructive inspection device and non-destructive inspection method using measurement principles described hereinafter.

Figure 1:
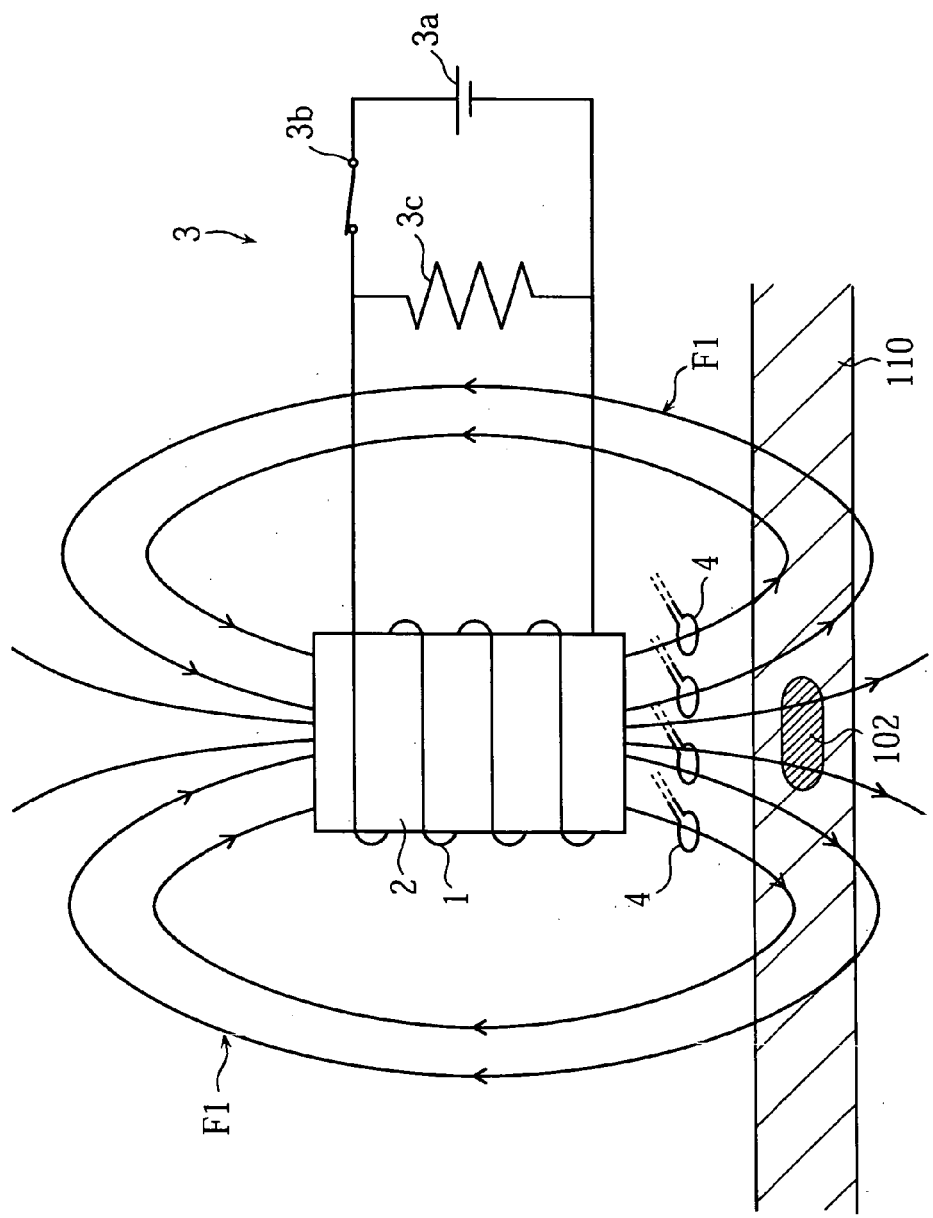
FIG. 1 is a conceptual view that shows the general composition of a device for carrying out non-destructive inspection using the application and shutting off of a static magnetic field, and also shows the operation of this device.
Figure 2:
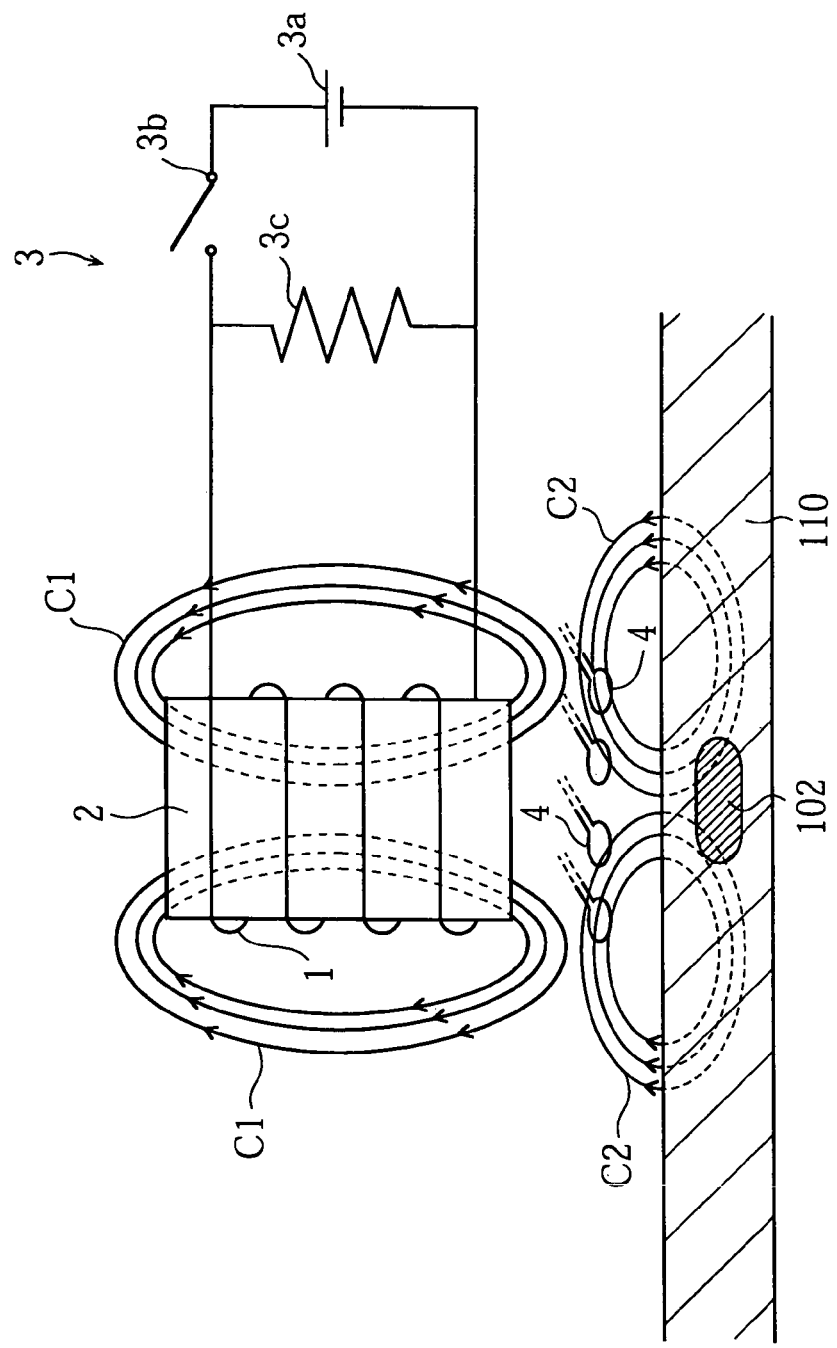
FIG. 2 is a further conceptual view that shows the general composition of a device for carrying out non-destructive inspection using the application and shutting off of a static magnetic field, and also shows the operation of this device.

FIG. 1 and FIG. 2 are conceptual views showing the general composition of a device for carrying out non-destructive inspection using the application and shutting off of a static magnetic field, and also showing the operation of this device. The non-destructive inspection device comprises an exciting coil 1 wound about an iron core 2, a drive circuit 3 for driving the exciting coil 1, and a plurality of sensor coils 4. The drive circuit 3 incorporates a DC power supply 3a, a switch 3b and a resistance 3c. The sensor coils 4 are loop coils. When carrying out inspection, this device is positioned in the vicinity of the inspection target. In FIG. 1 and FIG. 2, the device is positioned in the vicinity of the spot weld section of a steel plate member 110, formed by spot welding of two steel plates. A nugget section 102 exists inside this spot weld section.

As shown in FIG. 1, when the switch 3b is turned on, a static magnetic field F1 is applied to the spot weld section. More specifically, the switch 3b is turned on, a voltage output by the DC power supply 3a is applied to the exciting coil 1, and a DC current flows in the exciting coil 1, whereby a static magnetic field F1 is created surrounding the exciting coil 1. A portion of the static magnetic field F1 is formed inside the steel plate member 110. The location in which the magnetic field is formed in the steel plate member 110, in other words, the location through which the magnetic flux passes, is magnetized in accordance with the intensity of the magnetic field. In order to judge the suitability or unsuitability of the state of the welding in the spot weld section, on the basis of the size of the nugget section 102, the non-destructive inspection device is positioned in such a manner that the magnetic flux passes through the nugget section 102 when the static magnetic field is applied.

As shown in FIG. 2, when the switch 3b is turned off, the static magnetic field F1 is shut off. More specifically, when the switch 3b is turned off, the DC current that has been flowing in the exciting coil 1 until that point is shut off, and therefore the static magnetic field F1 is also shut off. Due to the shutting off of the static magnetic field F1, the loops of magnetic flux of the static magnetic field F1 separate into a closed loop C1 of magnetic flux in the region surrounding the exciting coil 1, and a closed loop C2 of magnetic flux in the region surrounding the steel plate member 110. The closed loop C1 rapidly declines and disappears. By contrast, the closed loop C2 does not disappear immediately, but rather declines in a gradual fashion, due to the sustaining action of the magnetic energy of the steel plate member 110, which is a magnetic body.

During the course of disappearance of the closed loop C2, the change in magnetic flux in the vicinity of the steel plate member 110 is detected by the respective sensor coils 4 positioned in the vicinity of the surface of the steel plate member 110. In an ideal situation, after the static magnetic field has been shut off, the change in magnetic flux detected by the sensor coils 4 decreases in a steady exponential fashion. However, in practice, the situation deviates from this ideal state of change. This deviation is thought to be caused by transient current which is induced in the steel plate member 110 by the change in the state of magnetization in the steel plate member 110, during the course of disappearance of the magnetic energy (residual magnetic field) accumulated in the steel plate member 110. Therefore, the model described below can be hypothesized for the change in the magnetic flux of the residual magnetic field after the static magnetic field has been shut off.

Figure 3:
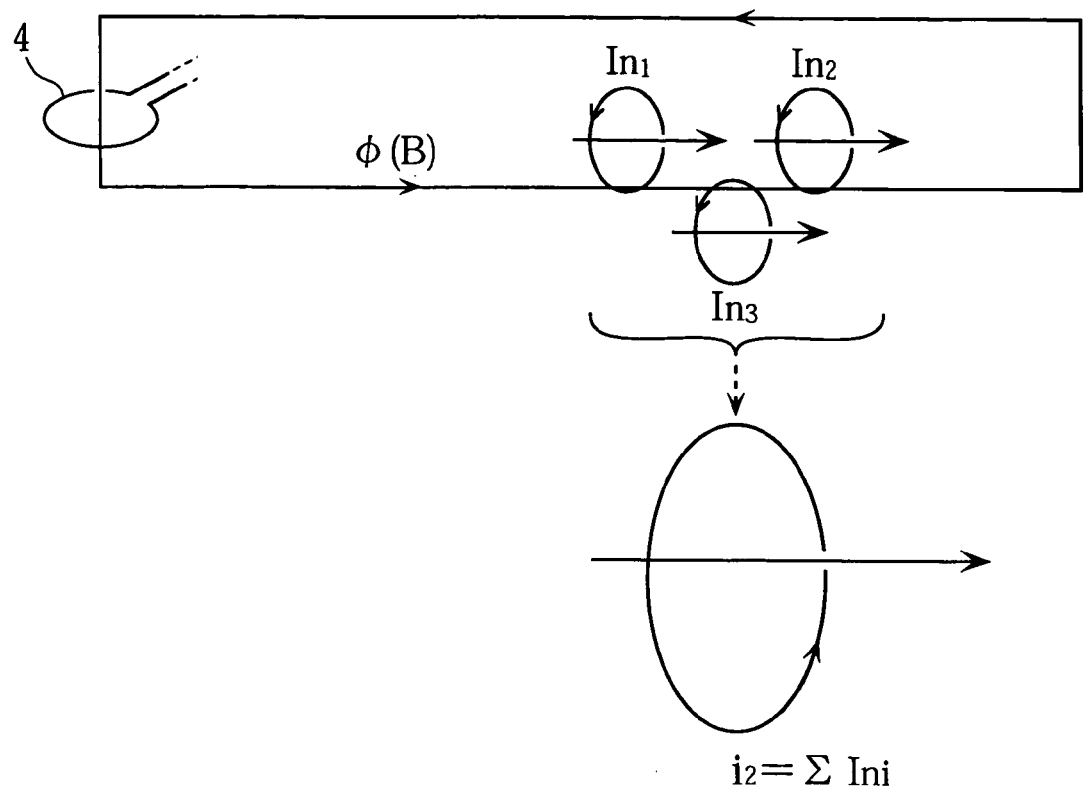
FIG. 3 shows a model of the course of disappearance of a closed loop of magnetic flux after shut off of a static magnetic field.

FIG. 3 shows a model of the course of disappearance of the residual magnetic field. In this course of disappearance, as illustrated in FIG. 3, the density of the magnetic flux Φ passing through one of the sensor coils 4 is denoted by B. Furthermore, the plurality of transient currents induced in the steel plate member 110 by the change in the magnetic flux density B are denoted by $In_1$, $In_2$, $In_3$, ..., and the coefficient of induction relating to these induced transient currents are denoted by $M_1$, $M_2$, $M_3$, .... The transient currents $In_1$, $In_2$, $In_3$, ... induced by the change in the magnetic flux density B are considered to be mutually independent. Here, the transient currents $In_1$, $In_2$, $In_3$, ... can be substituted by a single transient current $i_2$ induced by a coefficient of induction $M = \Sigma M_i$ ($i = 1, 2, 3, ...$) in accordance with the change in magnetic flux density B. Therefore, the course of disappearance of the magnetic flux Φ passing through any one sensor coil 4, can be expressed by the magnetic flux density B, and the transient current $i_2$ induced by the coefficient of induction M, due to the change in magnetic flux density B.

Figure 4:
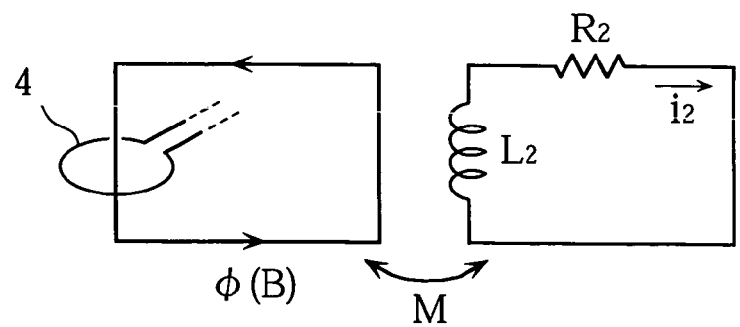
FIG. 4 shows an equivalent circuit relating to the transient current in FIG. 3.

FIG. 4 shows an equivalent circuit of FIG. 3. Here, $R_2$ shows the electrical resistance relating to the transient current $i_2$, and $L_2$ shows the inductance relating to the transient current $i_2$.

Figure 5:
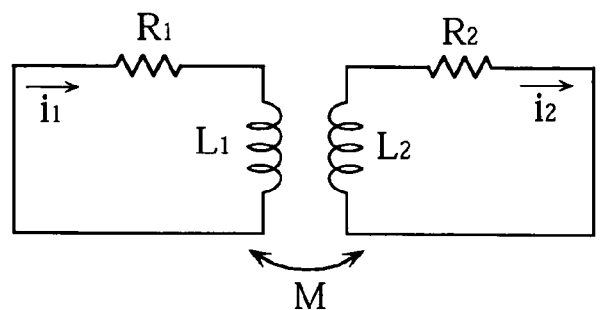
FIG. 5 illustrates the closed loop of magnetic flux density in FIG. 4, as converted into an equivalent magnetic circuit.

FIG. 5 is a diagram wherein the closed loop of magnetic flux Φ in the circuit diagram in FIG. 4 (the closed loop C2 passing through a single sensor coil 4 in FIG. 2) is substituted by an equivalent magnetic circuit. Here, $i_1$ corresponds to the magnetic flux density (B in FIG. 4). $R_1$ corresponds to a given irreversibility of the magnetic flux Φ. $L_1$ corresponds to the inductance of the magnetic circuit, which is a physical quantity directly proportional to the volume of the whole magnetic flux space maintaining the magnetic flux Φ. Moreover, in the circuit diagram shown in FIG. 5, the coefficient of induction M corresponds to the mutual inductance between the inductance $L_1$ of the magnetic circuit and the inductance $L_2$ of the transient current circuit.

Figure 6:
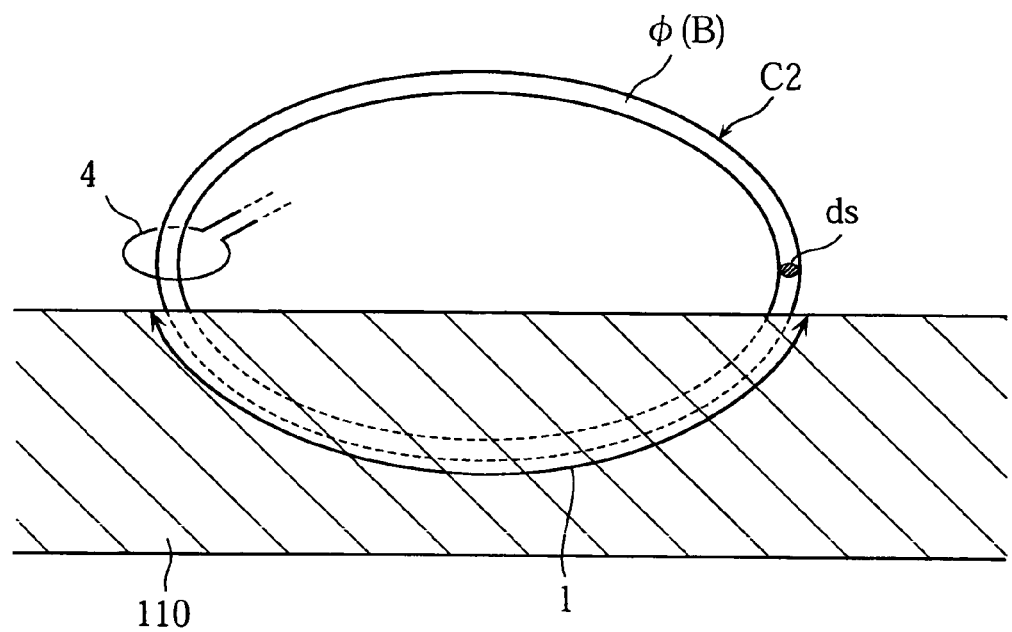
FIG. 6 shows a closed loop of magnetic flux passing through a single sensor coil immediately after shut off of a static magnetic field.

FIG. 6 shows a schematic view of the closed loop C2 having magnetic flux Φ (magnetic flux density B ($=i_1$)) passing through a single sensor coil 4, after the static magnetic field F1 has been shut off. As described previously, after shut off of the static magnetic field, the magnetic energy W accumulated in the steel plate member 110 during the application of the magnetic field declines gradually, rather than disappearing immediately. This magnetic energy W is maintained in the closed loop space of magnetic flux Φ, and it gradually disappears in accordance with the irreversibility $R_1$ of the magnetic flux Φ. In general, the magnetic energy W can be expressed by the following equation (1).

$$W = \frac{1}{2\mu} \int i_1^2 dv = \frac{1}{2} L i_1^2 \qquad (1)$$

Here, L is a value that is directly proportional to the volume of the space in which a magnetic flux of magnetic flux density i1 is maintained, in other words, the volume of the space in which the magnetic energy is maintained. On the other hand, Equation (1) is the same as the equation expressing the energy accumulated when a current of i1 flows in a coil of inductance L. Therefore, it can be seen that the inductance L1 in the circuit diagram shown in FIG. 5 is directly proportional to the volume of the total space in which the magnetic flux is maintained.

The equivalent circuit shown in FIG. 5 can be represented by Equation (2).

$$L_1 \frac{di_1}{dt} + R_1 i_1 - M \frac{di_2}{dt} = 0 \\ L_2 \frac{di_2}{dt} + R_2 i_2 - M \frac{di_1}{dt} = 0 \Bigg\} \quad (2)$$

If the simultaneous differential equations indicated in Equation (2) are solved for i1 and i2, then the following equations (3a) and (3b) are obtained as respective solutions.

$$i_1 = A_1 \exp\{-(\alpha - \gamma)t\} - A_2 \exp\{-(\alpha + \gamma)t\} \quad (3a)$$

$$i_2 = A_3 \exp\{-(\alpha - \gamma)t\} - A_4 \exp\{-(\alpha + \gamma)t\} \quad (3b)$$

$$\alpha = \frac{L_1 R_2 + L_2 R_1}{2(L_1 L_2 - M^2)}$$

$$\gamma = \frac{\sqrt{(L_1 R_2 - L_2 R_1)^2 - 4R_1 R_2 M^2}}{2(L_1 L_2 - M^2)}$$

$$A_1 = \frac{-(L_1 R_2 - L_2 R_1) - \sqrt{(L_1 R_2 - L_2 R_1)^2 + 4R_1 R_2 M^2}}{2R_1 \sqrt{(L_1 R_2 - L_2 R_1)^2 + 4R_1 R_2 M^2}}$$

$$A_2 = \frac{(L_1 R_2 - L_2 R_1) - \sqrt{(L_1 R_2 - L_2 R_1)^2 + 4R_1 R_2 M^2}}{2R_1 \sqrt{(L_1 R_2 - L_2 R_1)^2 + 4R_1 R_2 M^2}}$$

$$A_3 = \frac{-M}{\sqrt{(L_1 R_2 - L_2 R_1)^2 + 4R_1 R_2 M^2}}$$

$$A_4 = A_3$$

Here, the respective constants in equation (3a) and equation (3b) are determined for the initial conditions, wherein the magnetic flux density i1 (=B) is taken to be B 0 at the time that the static magnetic field F1 is shut off (t=0). In this case, assuming that the coefficient of induction M is low and the transient current i2 induced by change in the magnetic flux density i1 is very small, in other words, L1·L2>>M·M, then the following results are obtained.

$$\alpha - \gamma \approx \frac{R_1}{L_1} = \frac{1}{\tau_1} \quad (4a)$$

$$\alpha + \gamma \approx \frac{R_2}{L_2} = \frac{1}{\tau_2} \quad (4b)$$

$$A_1 \approx I_0 \approx -\frac{1}{R_1} \quad (4c)$$

$$A_2 \approx 0 \quad (4d)$$

$$A_3 \approx 0 \quad (4e)$$

$$A_4 \approx 0 \quad (4f)$$

If Equation (4a) and Equation (4b) are substituted into Equation (3a), and $i_1$ is substituted for B, then equation (5) is obtained.

$$B = A_1 \exp(-t/\tau_1) - A_2 \exp(-t/\tau_2) \quad (5)$$

Figure 7A:
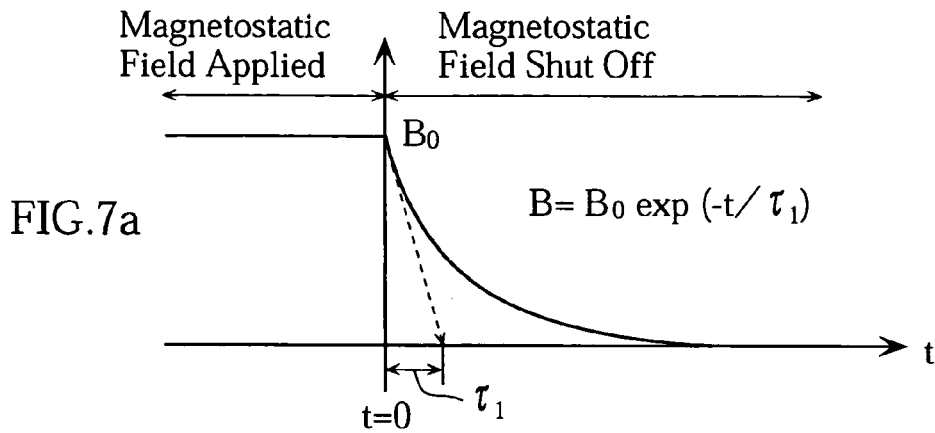
FIG. 7a–7d shows the transient change in respective physical quantities in the non-destructive inspection relating to the present invention.

Equation (5) indicates the transient change in the magnetic flux density B of the magnetic flux Φ passing through the sensor coil 4. Here, taking Equation (4d) into account, it is possible to ignore the second item on the right-hand side of Equation (5). Therefore, the change in the magnetic flux density B of the magnetic flux Φ forming the closed loop C2 shown in FIG. 6 can be approximated to the first item on the right-hand side of Equation (5) only. FIG. 7a indicates the transient change in the magnetic flux density B given by the first item on the right-hand side of Equation (5) only, after the time at which the magnetic field is shut off (t=0). The value of the magnetic flux density before t=0 indicates the magnetic flux density $B_0$ when the static magnetic field is being applied. On the other hand, the transient voltage actually detected by a sensor coil 4 during the course of disappearance of the magnetic field is equal to the rate of change of the magnetic flux density B with respect to time, in other words, the differential magnetic flux density dB/dt, multiplied by the cross-sectional area of the magnetic flux passing through the sensor coil 4. Therefore, by differentiating both sides of Equation (5) with respect to time t, Equation (6), in other words, an equation for the differential magnetic flux density, can be derived.

$$\begin{aligned} \frac{dB}{dt} &= -\frac{A_1}{\tau_1} \exp(-t/\tau_1) + \frac{A_2}{\tau_2} \exp(-t/\tau_2) \\ &= -\frac{A_1}{\tau_1} \left\{ \exp(-t/\tau_1) - \frac{A_2 \tau_1}{A_1 \tau_2} \exp(-t/\tau_2) \right\} \\ &= -\frac{A_1}{\tau_1} \{\exp(-t/\tau_1) - \exp(-t/\tau_2)\} \left( \because t=0, \frac{dB}{dt}=0 \rightarrow \frac{A_2 \tau_1}{A_1 \tau_2} = 1 \right) \\ &= -\frac{B_0}{\tau_1} \{\exp(-t/\tau_1) - \exp(-t/\tau_2)\} (\because A_1 \approx B_0) \\ &= -\frac{B_0}{\tau_1} \exp(-t/\tau_1) + \frac{B_0}{\tau_1} \exp(-t/\tau_2) \\ &\quad (= f_1(t) + f_2(t)) \end{aligned} \quad (6)$$

Figure 7B:
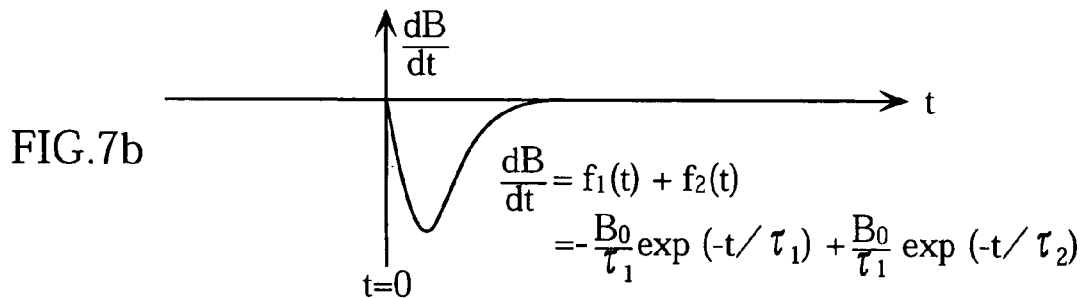

FIG. 7b shows the transient change in the differential magnetic flux density obtained by Equation (6). This waveform is known to coincide approximately with the waveform obtained when actual measurements are taken used a sensor coil 4 as a magnetic sensor. Therefore, it can be maintained that the model described with respect to FIG. 3 to FIG. 6 is an accurate reflection of the course of disappearance of the residual magnetic field. In other words, Equation (5) represents the change in the magnetic flux density B of the magnetic flux Φ passing through the sensor coil 4, and Equation (6) represents the differential change of the magnetic flux density dB/dt.

Figure 7C:
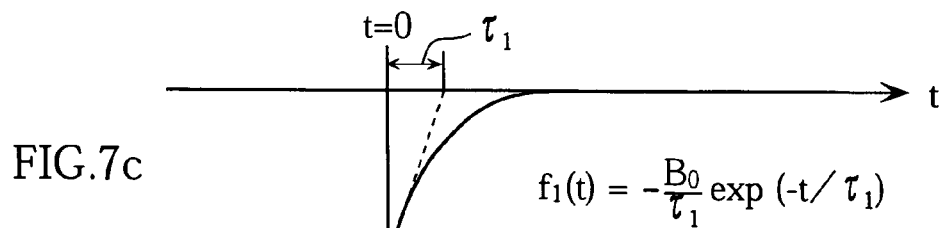

Here, it can be seen that term $\tau_1$ in the first item on the right-hand side of Equation (6) is equal to $L_1/R_1$, as can be deduced from Equation (4a), and therefore, it is equivalent to the time constant of the magnetic circuit of magnetic flux density $i_1$ (=B) shown in FIG. 5. Consequently, the first item on the right-hand side of Equation (6) represents ideal steady attenuation characteristics wherein the magnetic flux density B of the magnetic flux in the vicinity of the steel plate member 110 declines exponentially after the static magnetic field F1 has been shut off, in other words, it represents the ideal attenuation characteristics of the magnetic energy. Here, it is supposed that the time constant $\tau_1$ contained in the first item on the right-hand side of Equation (6) is called the "main time constant". FIG. 7c shows the attenuation characteristics of the magnetic energy expressed by the first item on the right-hand side of Equation (6) (the closed loop C2 of the magnetic flux Φ).

In order to determine the main time constant $\tau_1$, firstly, Equation (7) is obtained by taking the logarithm of either side of $f_1(t)$ expressed by the first item on the right-hand side of Equation (6). If Equation (7) is plotted on a graph, a straight line of gradient $1/\tau_1$ is obtained. Therefore $\tau_1$ can be determined from the gradient of the graph.

$$\ln f_1(t) = -\ln\frac{B_0}{\tau_1} + \frac{t}{\tau_1} \quad (7)$$

In the manner described above, it is possible to determine the main time constant of the transient change in the differential magnetic flux density of the residual magnetic field which disappears after the static magnetic field has been shut off. It has been confirmed experimentally that in a spot weld section, a change occurs at a time constant of $\tau_1$ in the nugget section in which a change in the metallic composition is produced by the temporary melting of the metal and in the region outside of this nugget section which does not undergo a change in the metallic composition. Therefore, by measuring and analyzing the distribution of the time constant $\tau_1$ in the spot weld section, it is possible to obtain information relating to the shape and dimensions of the portion where metallic composition has changed as in the nugget section.

Figure 7D:
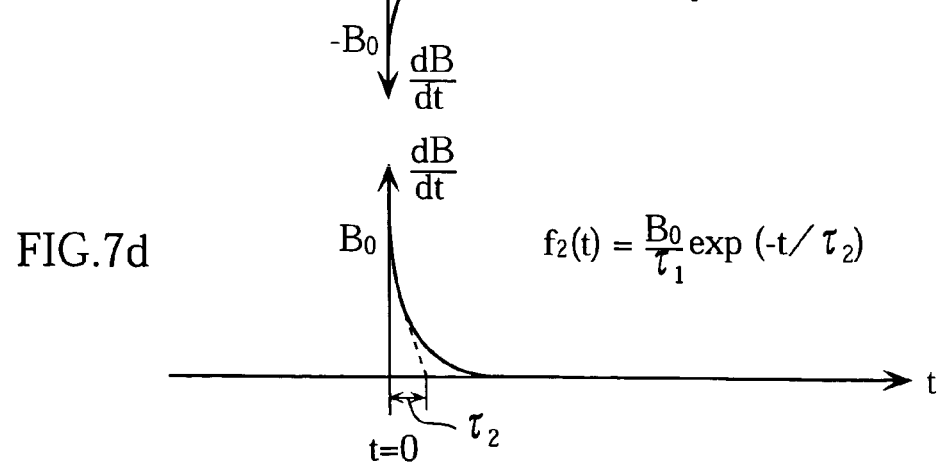

On the other hand, since the term $\tau_2$ of the second item on the right-hand side of Equation (6) is equal to $L_2/R_2$, as can be seen from Equation (4b), then it corresponds to the time constant of the equivalent circuit of the transient current $i_2$ shown in FIG. 5. Therefore, the second item on the right-hand side of Equation (6) represents the attenuation characteristics of the disappearance of transient current. FIG. 7d shows these attenuation characteristics of the disappearance of the transient current expressed by the second item on the right-hand side of Equation (6). It is assumed, here, that the term $\tau_2$ which is the time constant on the second item on the right-hand side of Equation (6) is known as the "secondary time constant". The method for determining $\tau_2$ is the same as that described above with respect to $\tau_1$. $R_2$ is the resistance relating to the transient current, in other words, it corresponds to the electrical resistance of the material at the location through which the transient current flows. Moreover, $L_2$ corresponds to the volume of the space magnetized by the transient current. As shown in FIG. 6, if the surface area through which the magnetic flux passes is taken to be ds, then the length of the magnetized region in the steel plate member 110 can be expressed by $L_2$ in Equation (8) below.

$$L_1 \propto \int dv = l \cdot ds \quad (8)$$

From Equation (4b) and Equation (8), it can be see that the time constant $\tau_2$ of the attenuation characteristics of the disappearance of the transient current is directly proportional to the length of the magnetic path generated by the transient current, in other words, the magnetic path passing through the steel plate, as illustrated in Equation (9) below.

$$\tau_2 \propto l \quad (9)$$

Therefore, the change in the length of the magnetic path 1 of the magnetic flux passing through in the vicinity of the spot weld section can be detected as a change in the time constant $\tau_2$ of the attenuation characteristics in the second item on the right-hand side of Equation (6).

Figure 8:
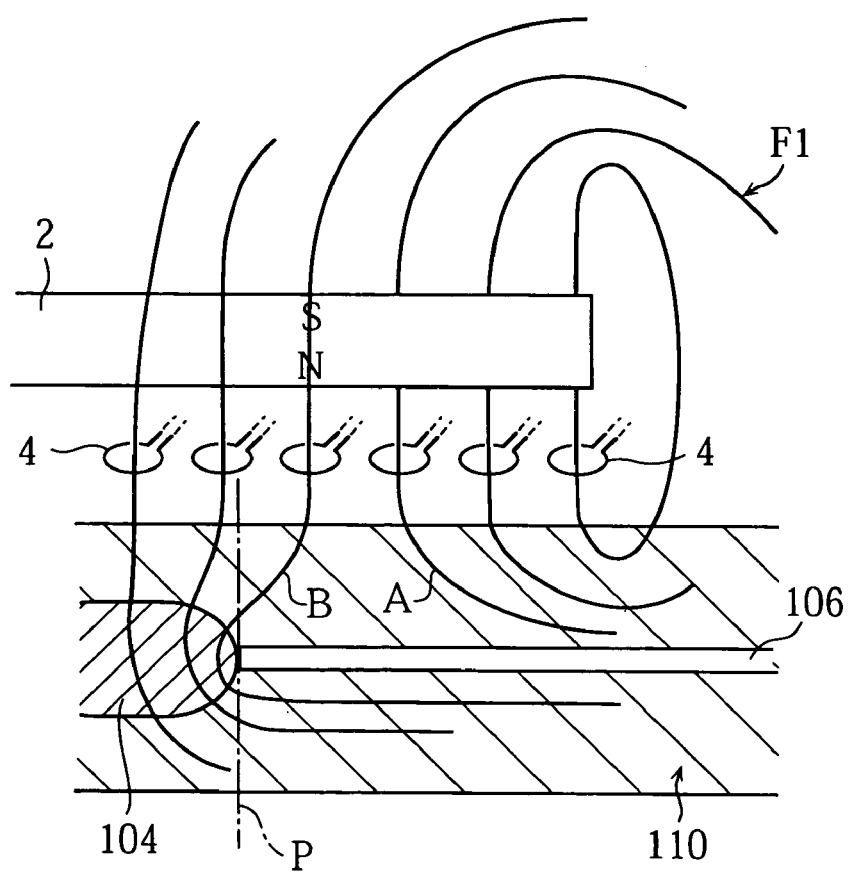
FIG. 8 shows the state of magnetic flux in the vicinity of the end portion of a joint section of a spot weld section.

FIG. 8 shows the vicinity of the end portion of a joint section 104 of the spot weld section during application of the static magnetic field. FIG. 8 shows a case where a larger number of sensor coils 4 are disposed in a linear arrangement, compared to FIG. 1 and FIG. 2. When the static magnetic field is being applied, the magnetic flux of the static magnetic field F1 in the vicinity of the boundary P between the joint section 104 and the gap section 106 takes the form shown in FIG. 8. In this case, there is a location in the vicinity of the end portion of the joint section 104 where the path of the magnetic flux divides significantly, in the leftward and rightward direction. For example, in FIG. 8, the magnetic flux line A passes over the gap section 106 between the steel plate members 110, but the magnetic flux line B passes through the joint section 104 and then to the lower side of the gap section 106. The magnetic flux lines are separated in this way due to the presence of the boundary P between the joint section 104 and the gap section 106. This difference in the magnetic path when a static magnetic field is being applied is also reflected in the residual magnetic field after the static magnetic field has been shut off. Therefore, if it is possible to find out the position at which the path of magnetic flux forming the residual magnetic field changes suddenly, then it is possible to estimate the position of the end of the joint section 104. Here, the difference between A and B appears as a difference in the length of the magnetic flux path, in other work, the length of the magnetic path.

Figure 9:
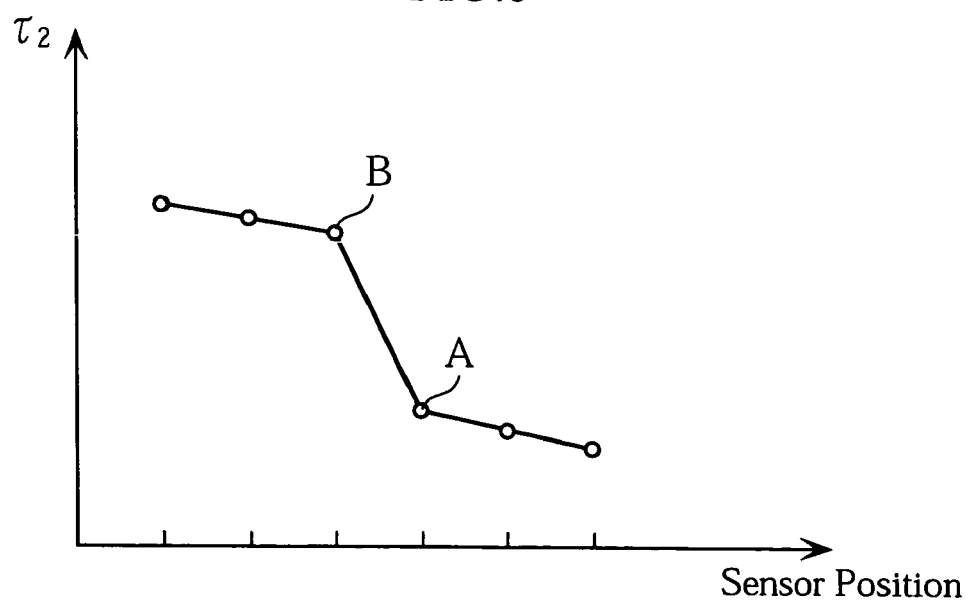
FIG. 9 shows the relationship between the distribution of a time constant $\tau_2$ in the attenuation characteristics of the disappearance of the transient current, and the position of the sensor coil.
Figure 24:
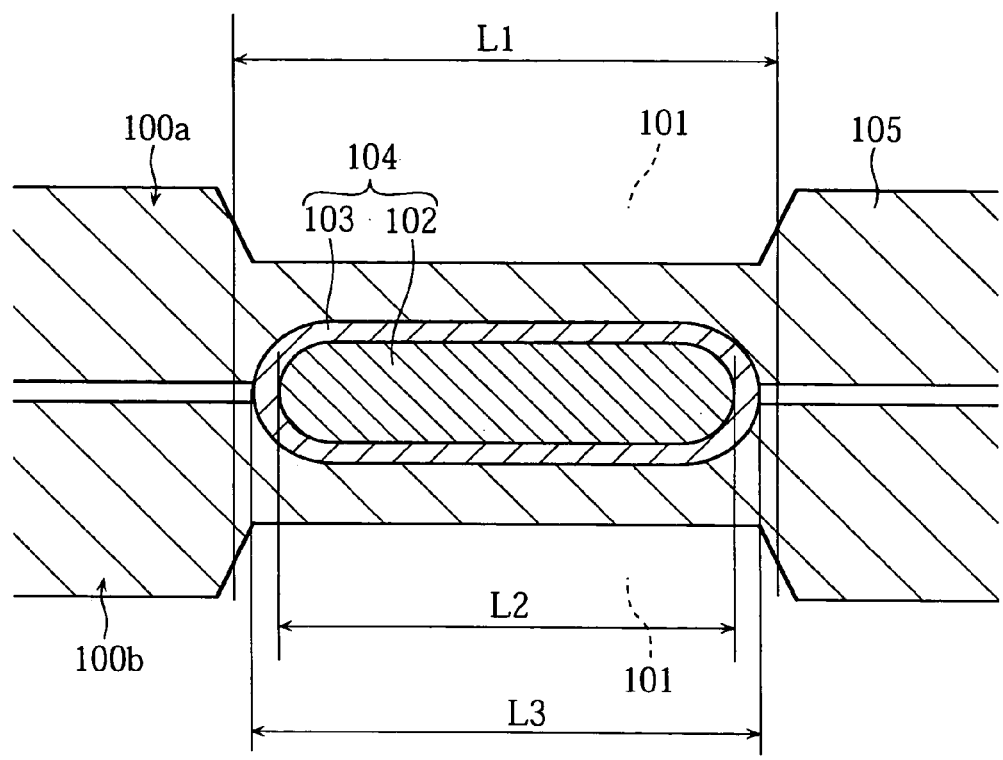
FIG. 24 is a cross-sectional view of a spot weld section in two metal plate joined by spot welding.
Figure 25:
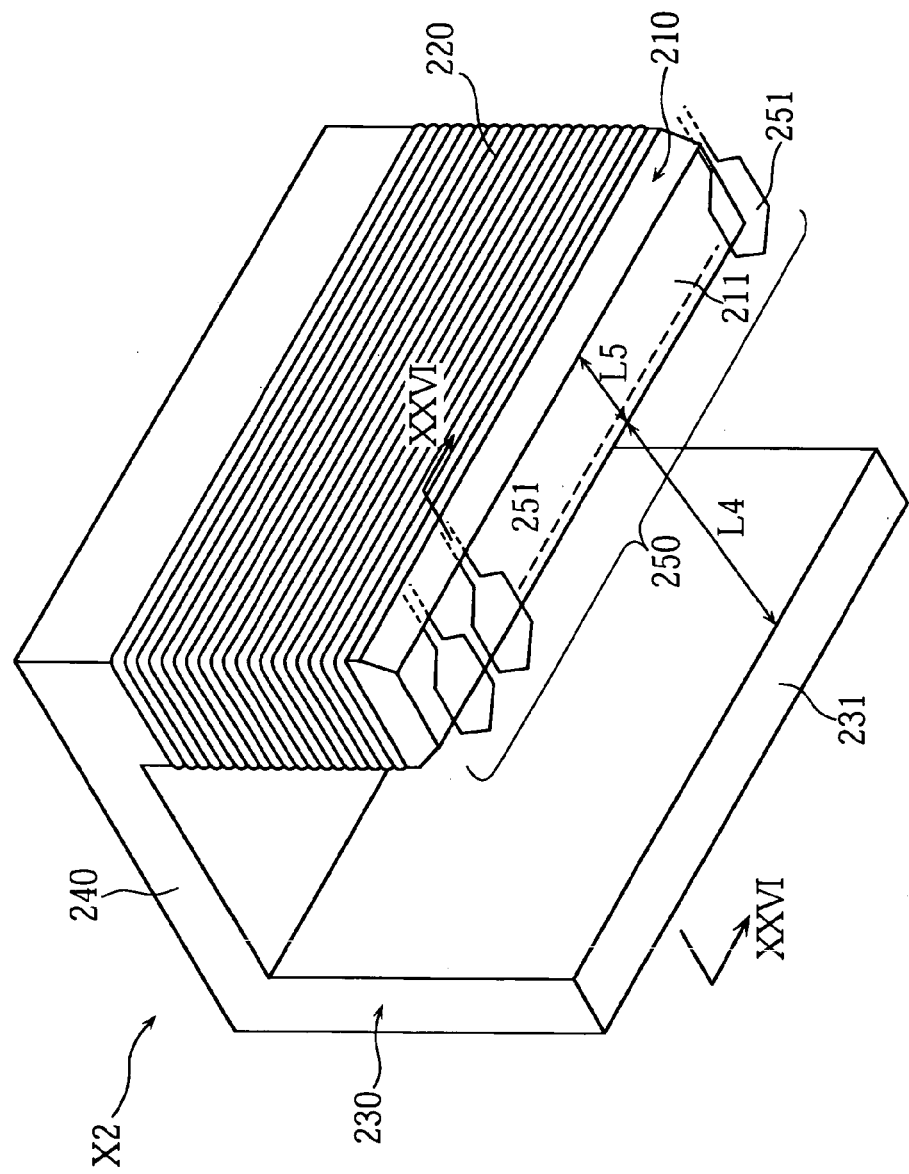
FIG. 25 shows a conventional non-destructive inspection device.
Figure 26:
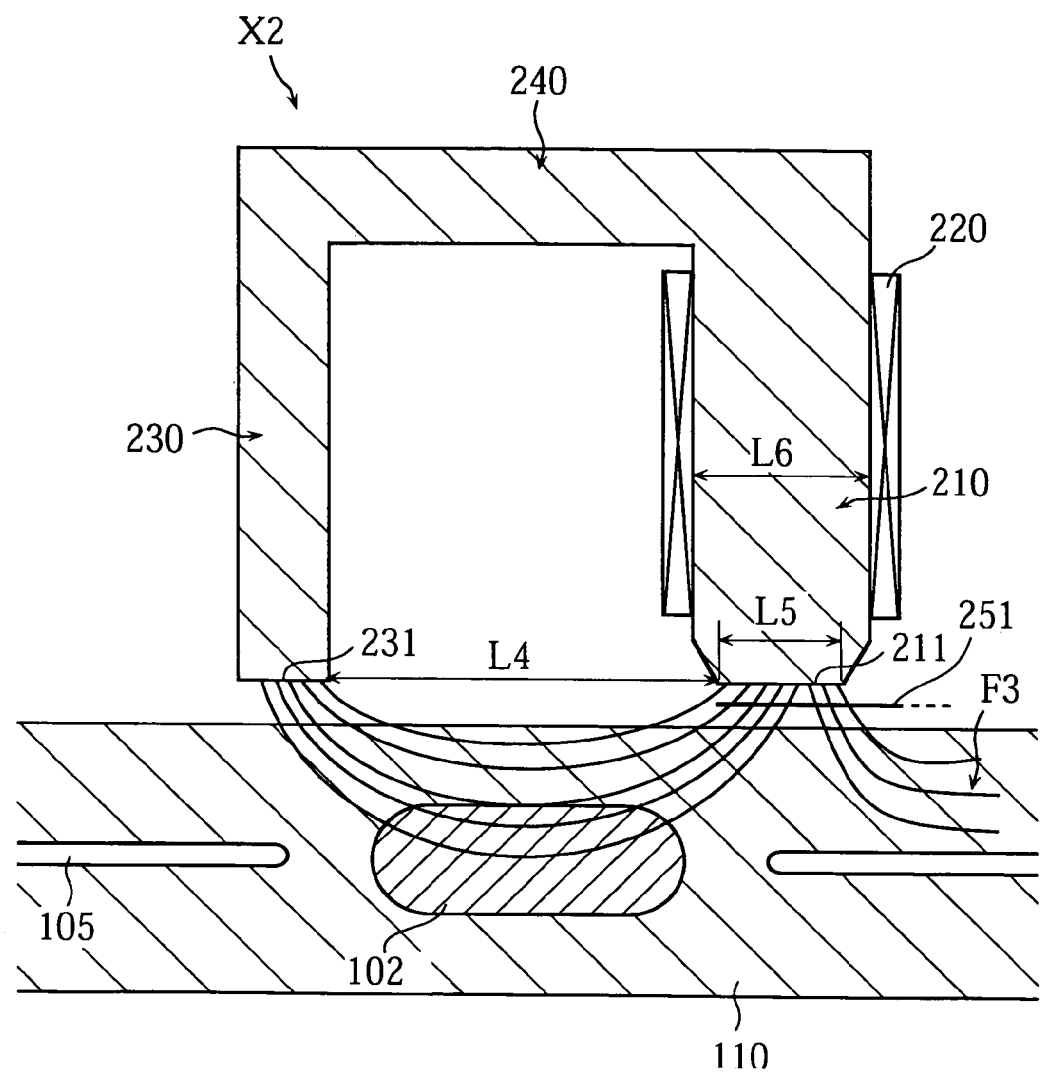
FIG. 26 shows a cross-section along line XXVI—XXVI in FIG. 25.

FIG. 9 shows how the distribution of the time constant $\tau_2$ in the attenuation characteristics for the disappearance of the transient current changes with respect to the position of the sensor coil 4. If a plurality of sensor coils 4 are disposed in the vicinity of the spot weld section of the steel plate members 110 and the time constant $\tau_2$ at the position of the each sensor coil 4 is measured, then it is possible to find the point of sudden change in the time constant as illustrated in FIG. 9, in other words, the point of sudden change in the magnetic path length. On the basis of this point of sudden change, it is possible to estimate the end of the joint section 104 as illustrated in FIG. 24, as a result of which, it is possible to infer the joint length L3 in the spot weld section.

Figure 10:
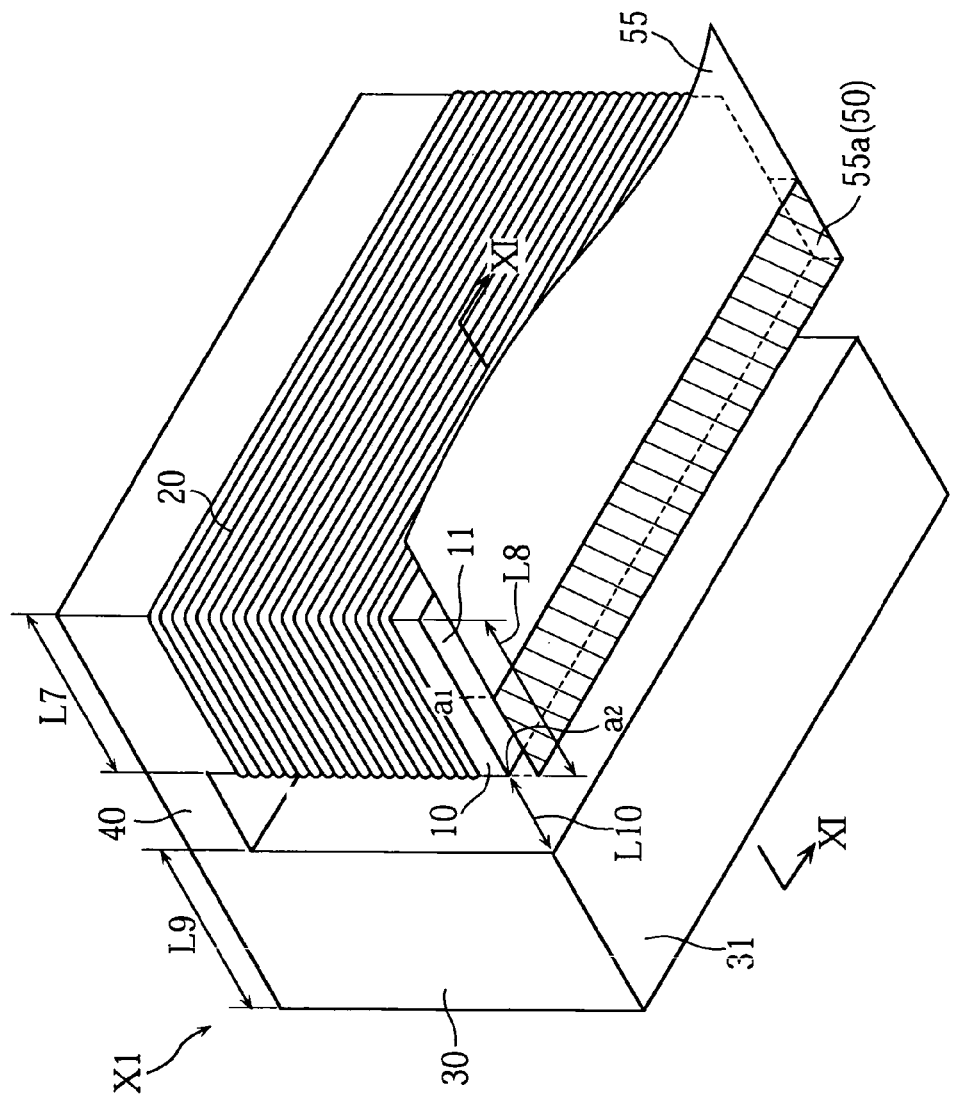
FIG. 10 is an oblique view of a non-destructive inspection device relating to the present invention.
Figure 11:
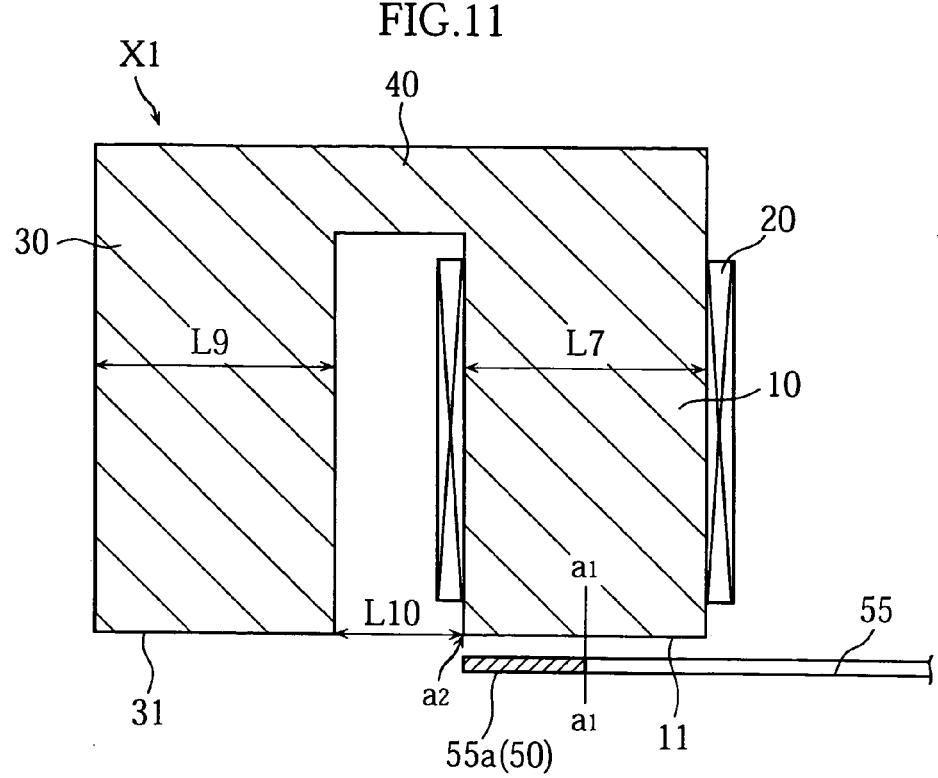
FIG. 11 is a cross-sectional view along line XI—XI in FIG. 10.

FIG. 10 shows a non-destructive inspection device X1 according to the present invention. FIG. 11 is a cross-sectional view along line XI—XI in FIG. 10. The non-destructive inspection device X1 is constituted as a device utilizing the measurement principles described above, involving the application and shutting off of a static magnetic field. The non-destructive inspection device X1 comprises an exciting pole 10, an exciting coil 20 wound about same, a recovering pole 30, a connecting section 40 connecting the exciting pole 10 and the recovering pole 30, and a coil array 50 disposed in the vicinity of the exciting section 10.

The exciting pole 10 is an iron core for increasing the magnetic flux density of the magnetic field induced by the passing of current in the exciting coil 20, and it is formed integrally with the recovering pole 30 by means of the connecting section 40. The exiting pole 10 has a magnetic flux exciting surface 11 on the front end thereof. The width L7 of the trunk portion of the exciting pole 10 is the same as the width L8 of the magnetic flux exciting surface 11. In the present embodiment, the width L7 and the width L8 are 3.0 to 5.0 mm. The width L9 of the trunk portion of the recovering pole 30 is the same as the width L7 of the trunk portion of the exciting pole 10, and is therefore between 3.0 and 5.0 mm. The recovering pole 30 has a recovering surface 31 on the front end thereof. The magnetic flux excited from the magnetic flux exciting surface 11 of the exciting pole 10 is recovered at the recovering surface 31. The recovering surface 31 has a similar shape to the magnetic flux exciting surface 11 of the exciting pole 10. The distance of separation L10 between the recovering surface 31 and the magnetic flux exciting surface 11 is shorter than in the prior art, and in the present embodiment, it is 1.0 to 2.0 mm.

The coil array 50 comprises a plurality of loop coils (shown approximately in FIG. 10 and FIG. 11), and detects the change in magnetization in the vicinity of the inspection target, during application of a static magnetic field and after shut off of the magnetic field, outputting this difference in the form of a voltage. The respective loop coils are made from a conductive material, such as copper, or the like, and are patterned onto a flexible substrate 55. The coil array 50 is formed in a coil array forming section 55a (indicated by the diagonal hatching) on the flexible substrate 55.

Figure 12:
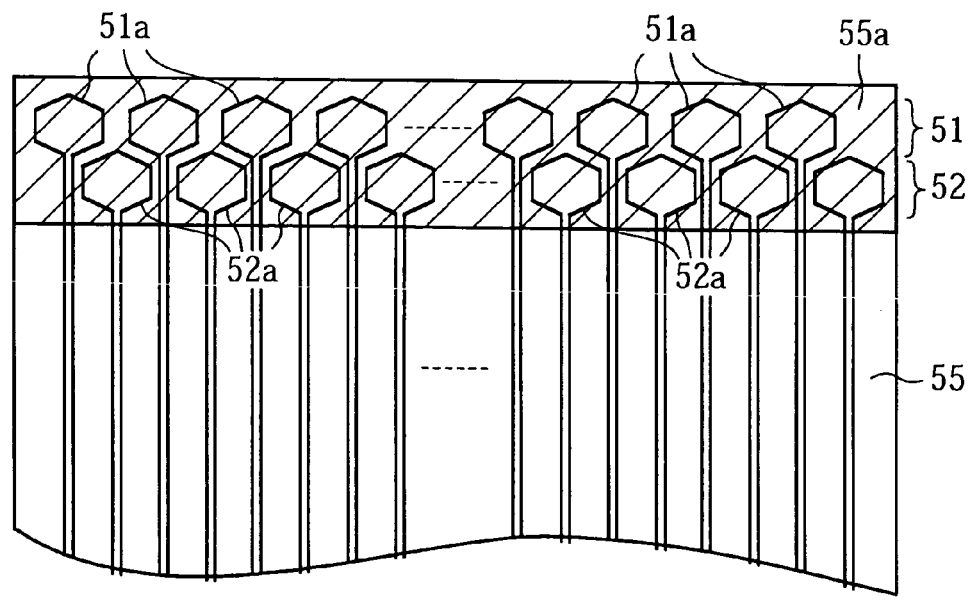
FIG. 12 shows a coil array patterned onto a flexible substrate.

The flexible substrate 55 is disposed in such a manner that the coil array forming section 55a opposes the magnetic flux exciting surface 11. FIG. 12 shows a coil array 50 formed by patterning on a flexible substrate 55. The coil array 50 consists of a first coil row 51 wherein 16 loop coils 51a forming magnetic sensors are arranged in a row, and a second coil row 52 wherein a further 16 loop coil 52a are similarly arranged in a row. As illustrated in FIG. 10 and FIG. 11, the coil array 50 formed in the coil array forming section 55a is maintained at a prescribed interval from the magnetic flux exciting surface 11, directly below the magnetic flux exciting surface 11, and the first and second coil rows 51, 52 are disposed in such a manner that they extend in the longitudinal direction of the magnetic flux exciting surface 11. Furthermore, the coil array 50 is disposed such that it is offset toward the recovering pole 30, with respect to the magnetic flux exciting surface 11. More specifically, the coil array 50 according to the present embodiment is disposed such that opposes a region from the center $a_1$ of the magnetic flux exciting surface 11 in the width direction thereof, to the edge portion $a_2$ of the side thereof nearest to the recovering pole 30.

Figure 13:
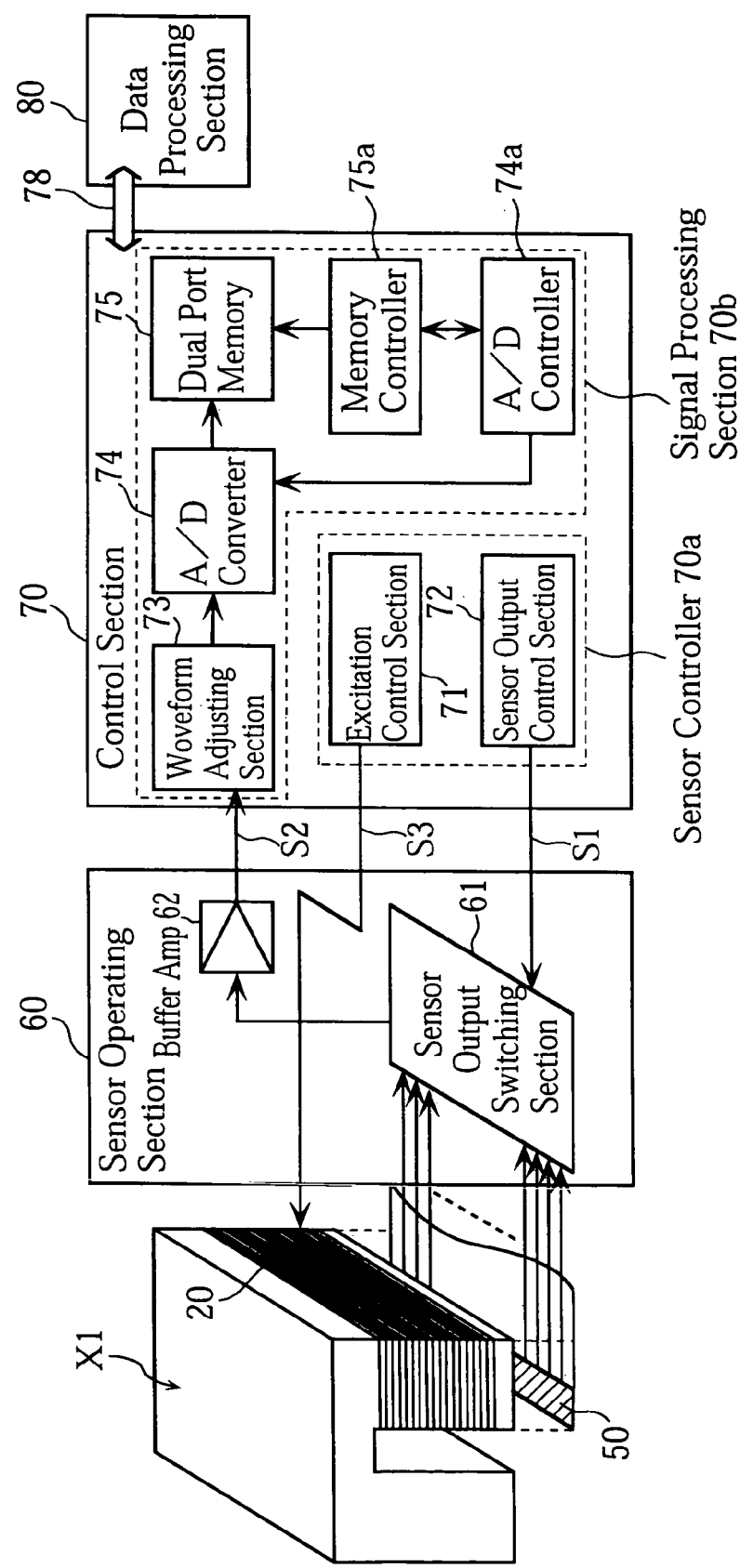
FIG. 13 shows the composition of a system for operating the non-destructive inspection device shown in FIG. 10.

FIG. 13 shows the composition of a system for operating the non-destructive inspection device X1. This system comprises a sensor operating section 60, a control section 70 and a data processing section 80.

The sensor operating section 60 comprises a sensor output switching section 61 and a buffer amp 62. The sensor output switching section 61 is a circuit for selecting only one output of the respectively outputs of the plurality of loop coils 51a, 52a constituting the coil array 50, and outputting same to the buffer amp 62. The sensor output switching section 61 selecting the outputs of the respective loop coils 51a, 52a, sequentially, and outputs same to the buffer amp 62, in accordance with a 4-bit sensor output switching signal S1. The buffer amp 62 is a buffer circuit for outputting the output signal from the sensor output switching section 61 to the control section 70, in the form of a detection signal S2.

The control section 70 is formed by a control circuit connected via a generic bus 78 to the data processing section 80, and it comprises a sensor control section 70a and a signal processing section 70b. The sensor control section 70a comprises an excitation control section 71 and a sensor output control section 72. The signal processing section 70b comprises a waveform adjusting section 73, an A/D converter 74, a dual port memory 75, an A/D controller 74a, and a memory controller 75a. The control section 70 is formed on a control substrate connected to a generic slot of a computer.

The excitation control section 71 of the sensor control section 70a outputs a drive signal S3 to the excitation coil 20, in order to generate or shut off a static magnetic field of a prescribed intensity. In other words, the excitation control section 71 applies and shuts off a prescribed voltage, to the excitation coil 20. The sensor output control section 72 outputs a 4-bit sensor output switching signal S1 for sequentially selecting the output from the plurality of loop coils 51a, 52a contained in the coil array 50, to the sensor output switching section 61.

The waveform adjusting section 73 of the signal processing section 70b adjusts the detection signal S2 from the buffer amp 62, in accordance with the input specification of the A/D converter 74. The A/D converter 74 converts the input detection signal fro analog to digital. The dual port memory 75 stores the digital data after A/D conversion. The A/D controller 74a controls the timing of the A/D converter 74. The memory controller 75a controls the operations of writing to and reading from the dual port memory 75.

If the inspection target is a steel plate, then the effects of the eddy current loss appear notably in the transient change characteristics of the detection signal S2 after approximately 10 µs or less from the shut off of the static magnetic field (the average value being approximately 3 to 6 µs). Taking account of this fact, and the accuracy of data processing, it is desirable that the A/D converter 74 has a conversion speed of 4 Msps or above, and a conversion accuracy of 12 bits, or more.

The data processing section 80 is realized by means of a general computer having non-illustrated CPU and main memory. In the data processing section 80, the nugget diameter of the spot weld section is found by processing detection data output by the sensor operating section 60 and processed by the signal processing section 70b. The data processing section 80 comprises a monitor for displaying various measurement waveforms and measurement data tables. The various types of data processing described hereinafter are achieved by executing a computer program stored in a main memory (storage medium) by a CPU in the data processing section 80.

Next, one example of an inspection that can be carried out by means of the non-destructive inspection device X1 will be described with reference to FIG. 13 and FIG. 14a to FIG. 14c.

Figure 14A:
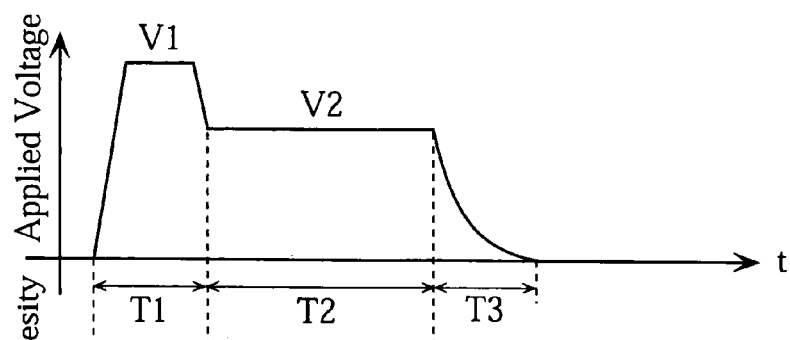
FIG. 14a–FIG. 14c respectively show the change in applied voltage, the change in magnetic flux density, and the change in output voltage (change in differential magnetic flux density), when the non-destructive inspection device illustrated in FIG. 10 is operated.
Figure 14B:
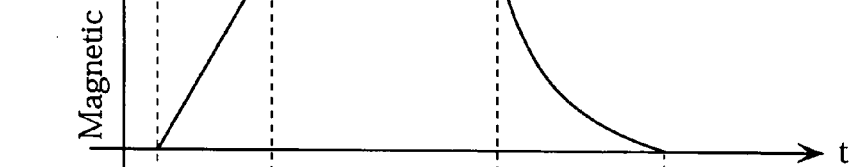

Firstly, the application and shutting off of the static magnetic field will be described. As described above, the generation and shutting off of the static magnetic field on the basis of the exciting coil 20 is controlled by outputting a drive signal S3 from the excitation control section 71 illustrated in FIG. 13. When the static magnetic field is applied, firstly, the drive signal S3 is set to a high-voltage signal V1 for time period T1, as shown in FIG. 14a, in order rapidly to generate a static magnetic field. Thereupon, in order to maintain a stable magnetic flux density inside the measurement object, the drive signal S3 is set to a low voltage signal V2 for the necessary time period T2. Thereafter, in order to shut off the static magnetic field, the drive signal S3 is shut off for a shut-off time period T3. If the inspection target is a steel plate, then the shut-off time period T3 should be approximately 3 to 6 µs, for example. FIG. 14b shows the change over time of the magnetic flux density of the static magnetic field created by the drive signal S3, in other words, by the application of a voltage.

Figure 14C:
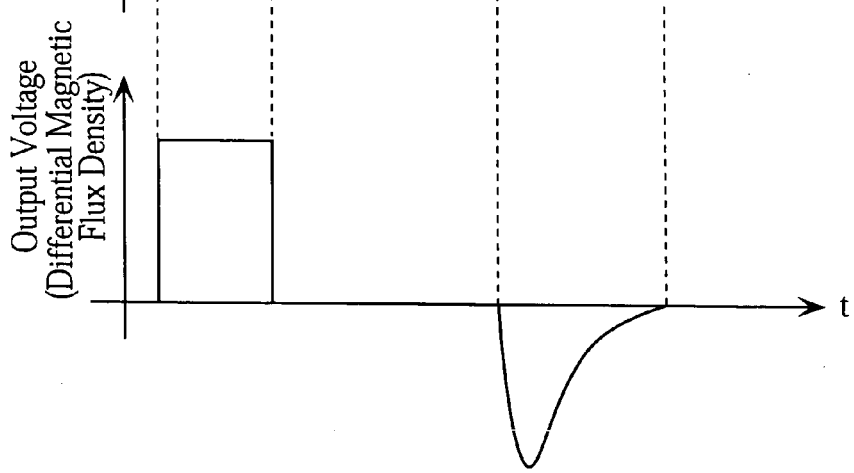

Next, the operation of measuring the change in magnetization will be described. During the course of generating and shutting off the static magnetic field, the changes in magnetic flux in the vicinity of the inspection target are measured by the coil array 50 of the non-destructive inspection device X1. Firstly, a sensor output switching signal S1 is output by the sensor output control section 72, thereby selecting one set of loop coils 51a, 52a in the coil array 50. Thereupon, the static magnetic field is applied and then shut off, as described above, and the output voltage from selected set of loop coils 51a, 52a is detected. FIG. 14c shows the change in output thus obtained from one of the loop coils. This change in output voltage corresponds to the change in the time differential of the magnetic flux density. This output is processed by the signal processing section 70b as detection signal S2. This measurement of the change in magnetic flux is carried out sequentially for all of the loop coils 51a, 52a. In the signal processing section 70b, the detection signal S2 is converted to 12-bit digital data by the A/D converter 74, at a conversion rate of 4 Msps, and is stored in the dual port memory 75.

In this way, measurement data is obtained for each of the loop coils 51a, 52a, whereupon the data processing section 80 illustrated in FIG. 13 processes the detection data from the respective loop coils 51a, 52a stored in the dual port memory 75 and determines the data required for identifying the nugget diameter, and the like.

Figure 15:
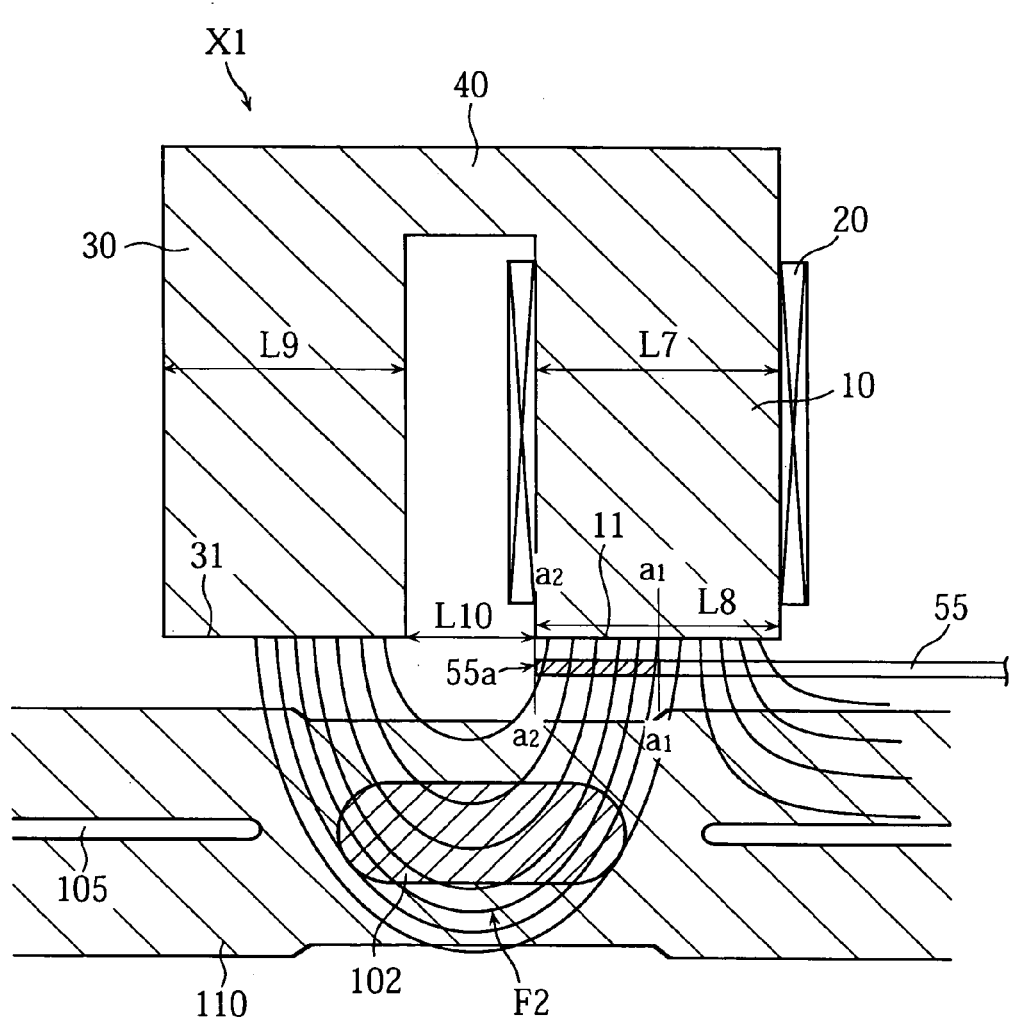
FIG. 15 shows a state where a static magnetic field is applied by means of the non-destructive inspection device illustrated in FIG. 10.

FIG. 15 illustrates the aforementioned measurement operation in a state where a static magnetic field F2 has been applied to the spot weld section by means of the non-destructive inspection device X1. In the non-destructive inspection device X1 according to the present invention, the coil array 50 patterned onto the coil array forming section 55a of the flexible substrate 55 is disposed in such a manner that it is offset toward the recovering pole 30, with respect to the magnetic flux exciting surface 11 of the exciting pole 10. More specifically, the coil array 50 according to the present embodiment is disposed in a position opposing a region from the center $a_1$ of the magnetic flux exciting surface 11 in the width direction thereof, until the edge region $a_2$ on the side thereof nearest to the recovering pole 30. The magnetic flux excited from the magnetic flux exciting surface 11 divides into a component which heads toward the recovering pole 30, in other words, a component which passes through the nugget section 102 in the spot weld section and the vicinity thereof, and a component which heads in the opposite direction, but since the coil array 50 is disposed in a position that is offset toward the recovering pole 30 with respect to the magnetic flux exciting surface 11, then the coil array 50 is able to trace the change in the magnetic flux passing through the nugget section 102, in a satisfactory manner. Consequently, the S/N ratio is improved and highly reliable inspection results can be obtained.

Moreover, in the non-destructive inspection device X1, the width L8 of the magnetic flux exciting surface 11 is the same as the width L7 of the trunk portion of the exciting pole 10, being some 3.0 to 5.0 mm. Therefore, when the static magnetic field is applied, the magnetic flux is excited from a magnetic flux exciting surface 11 having a larger surface area than in the prior art, and consequently, the inspection target can be magnetized satisfactorily.

Furthermore, in the non-destructive inspection device X1, the magnetic flux exciting surface 11 of the exciting pole 10 and the recovering surface 31 of the recovering pole 30 have the same shape, and therefore, the same surface area. Consequently, the magnetic flux density of the total magnetic flux excited from the magnetic flux exciting surface 11 is approximately the same as the magnetic flux density of the total magnetic flux recovered at the recovering surface 31, and hence a stable static magnetic field F2 can be formed.

Furthermore, in the non-destructive inspection device X1, the distance of separation L10 between the magnetic flux exciting surface 11 and the recovering surface 31 is shorter than in the prior art, at some 1.0 to 2.0 mm. Therefore, when the static magnetic field is shut off, the distance to be traveled by the residual magnetic field passing through the region other than the nugget section 102 is shorter than in the prior art, and hence noise is not liable to be incorporated in the course of the disappearance of the residual magnetic field. Therefore, it is possible to obtain information relating to the nugget section 102 that is satisfactory from the viewpoints of accuracy and S/N ratio.

Furthermore, in the non-destructive inspection device X1, the coil array 50 consists of two rows of coils 51, 52, aligned in the width direction of the magnetic flux exciting surface. Therefore, as shown in FIG. 15, it is possible to detect the change in magnetization across a broader range in the depth direction of the inspection target, and with a higher resolution.

Figure 16:
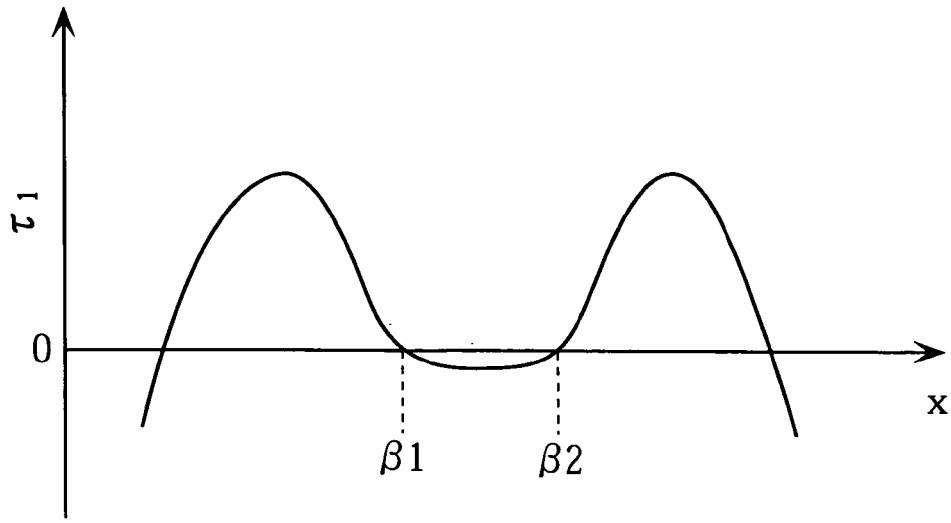
FIG. 16 shows an analytical graph (second-order differential curve of approximation curve) determined on the basis of $\tau_1$.

Next, a method for determining the nugget diameter by means of the non-destructive inspection device X1 will be described. Firstly, a total of 16 values for $\tau_1$ are determined for the position of each loop coil, on the basis of the detection signals S2 from all of the loop coils 51a contained in the first coil row 51 or all of the loop coils 52a contained in the second coil row 52. If the coil position is plotted on the horizontal axis and the time constant $\tau_1$ on the vertical axis, then the change data for the time constant $\tau_1$ corresponding to each loop coil position will be represented by a step-shaped function. The approximation curve f(x) for this step function is found by using the minimum square method. In this case, preferably, a sixth-order or higher approximation equation is used, in consideration of the approximation accuracy of the approximation curve. However, the equation is not limited to being a sixth-order equation or higher, and a fifth-order or lower equation may be used, according to the approximated waveform shape. Since the point of sudden change in $\tau_1$ is represented by a turning point in the approximation curve f(x), the first-order differential f'(x) and the second-order differential f''(x) of the approximation curve can be determined. FIG. 16 shows one example the second-order differential f''(x), in other words, an analytical graph. The solutions for f''(x)=0 which produce maximum and minimum points when substituted into f'(x), namely, β1 and β2, are determined. The positions of β1 and β2 are the positions at which $\tau_1$ changes suddenly due to the effects of the change in metallic composition in the nugget section. Therefore, the nugget diameter L2 can be determined from Equation (10) below. In a similar manner to the foregoing description, the joint diameter L3 can be determined from the change data for the time constant $\tau_2$ relating to the respective loop coil positions, and the indentation length L1 can be determined from the change data for the static magnetic field density when the static magnetic field is being applied.

$$L_2 = |\beta 1 - \beta 2| \quad (10)$$

Figure 17:
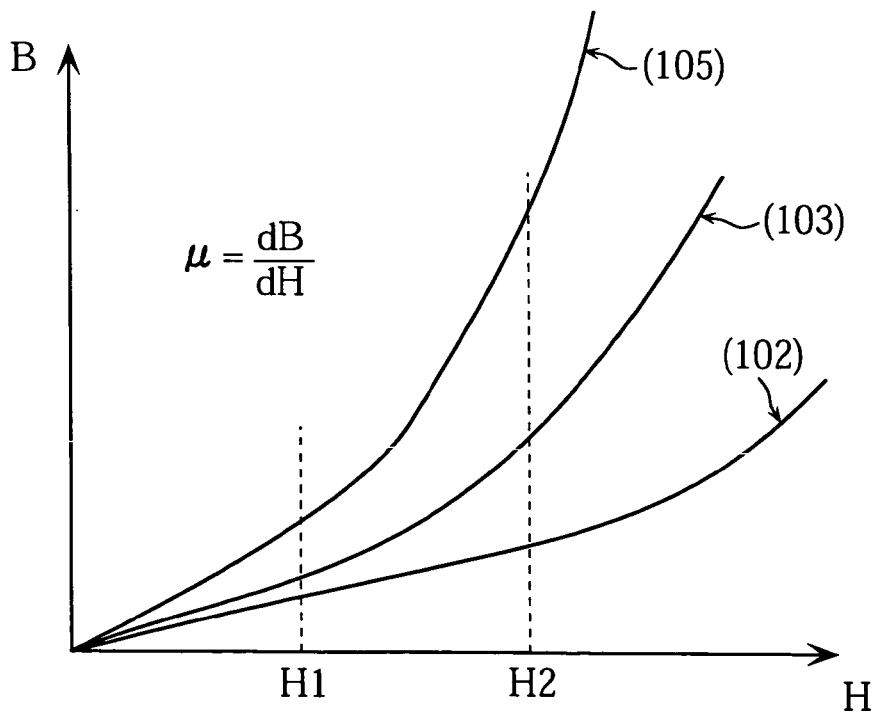
FIG. 17 shows the magnetic flux density with respect to applied magnetic field, for respective position forming a spot weld section.

Next, a further method for determining the nugget diameter by means of the non-destructive inspection device X1 shall be described. The second-order differential f''(x) of the approximation curve f(x) obtained from the series of $\tau_1$ data corresponding to the loop coil position contained in a single coil row has the shape illustrated in FIG. 16, as described previously. On the other hand, it is found on the basis of experimentation that there is a general relationship, as illustrated approximately by the graph shown in FIG. 17, linking the magnetizing force or magnetic field H between the nugget section 102, the pressure bonded section 103 and the original material 105, and the magnetic flux density B generated by that magnetic field. The ratio dB/dH, in other words, the gradient of the graph in FIG. 17, corresponds to the magnetic permeability μ. In the graph in FIG. 17, there is virtually no change in the magnetic permeability μ of the nugget section 102, between the magnetic field H1 and the magnetic field H2. However, the magnetic permeability $\mu$ of the pressure bonded section 103 and the original material 105 becomes larger as the magnetic field increases from H1 to H2. The value of $\tau_1$ is directly proportional to the inductance $L_1$ according to the measurement principles described above, and since $L_1$ is directly proportional to the magnetic permeability $\mu$ of the region through which $L_1$ passes, then it follows that $\tau_1$ is also directly proportional to the magnetic permeability $\mu$. Therefore, the rate of change of $\tau_1$ is the same as the rate of change of the magnetic permeability $\mu$, and hence finding the distribution function for $\tau_1$ corresponds to finding the distribution function for the magnetic permeability $\mu$.

Figure 18:
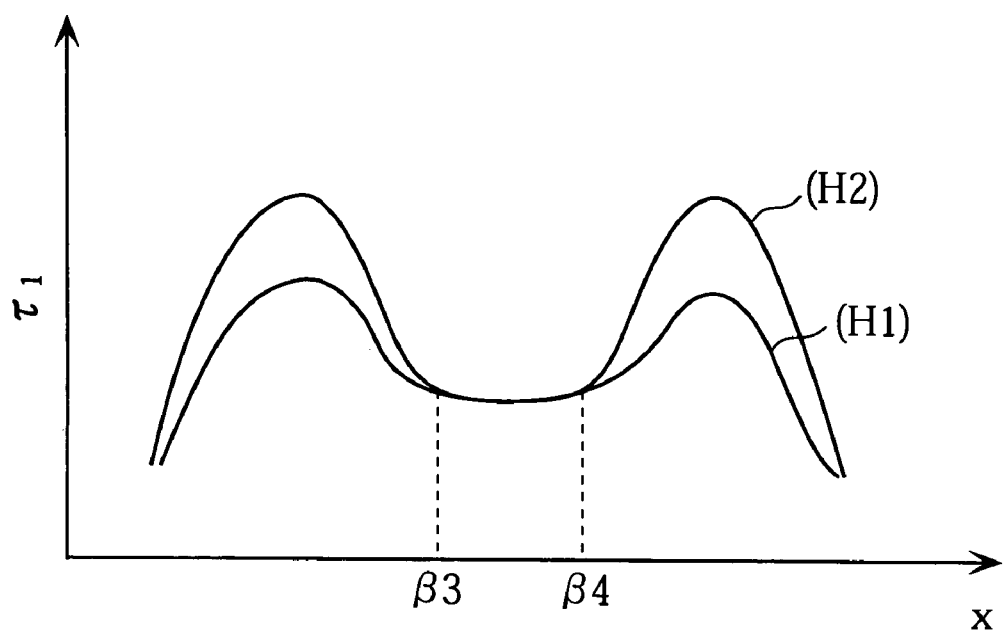
FIG. 18 shows two analytical graphs determined by means of a non-destructive inspection method relating to the present invention.

Therefore, by suitably adjusting the voltage of the power supply, two sets of measurements are carried out, in a case where a magnetic field of H1 is applied, and a case where a magnetic field of H2 is applied, using the first coil row 51 or the second coil row 52, of the non-destructive inspection device X1. H1 and H2 are magnetic fields which produce hardly any change in the magnetic permeability $\mu$ of the nugget section 102, similarly to the graphs shown in FIG. 17. If the two analytical graphs for $\tau_1$ based on the respective magnetic fields H1, H2 (namely, the second-order differential graphs of the approximation curves for $\tau_1$) are determined, then as shown in FIG. 18, there is a portion $\beta 3$–$\beta 4$ where these two graphs are overlapping, or are mutually parallel. The horizontal axis of the graph in FIG. 18 shows a position that is different to that in FIG. 16. The two analytical graphs in FIG. 18 show that there is no significant change in magnetic permeability, even when there is a change in the magnetic field, in the portion $\beta 3$–$\beta 4$ of the spot weld section. The remaining portions show a large change in magnetic permeability, due to change in the magnetic field. In other words, at the same depth from the surface of the inspection target, the $\beta 3$–$\beta 4$ portion corresponds to the nugget section 102, and the other portions correspond to the pressure bonded section 103 and the original material 105. It has been confirmed experimentally that the nugget diameter can be inferred more accurately by taking the distance between $\beta 3$ and $\beta 4$ to be the nugget diameter L2, rather than inferring the nugget diameter L2 from a single analytical graph. Therefore, according to a method of this kind, it is possible to perform highly reliable inspection with respect to the suitability or unsuitability of the welded state of a spot weld section.

By carrying out any of the aforementioned nugget diameter measurement methods, simultaneously, using the two respective coil rows 51, 52, it is possible to obtain a greater amount of information relating to the nugget section 102.

Figure 19:
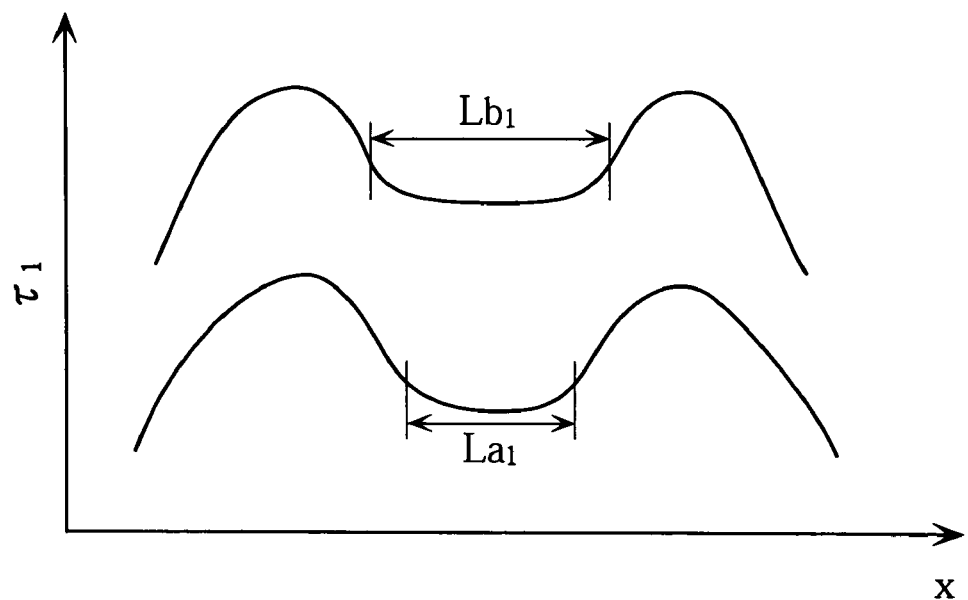
FIG. 19 shows one example of detection results in a case where two coil rows of a non-destructive inspection device relating to the present invention are operated in a combined fashion.
Figure 20:
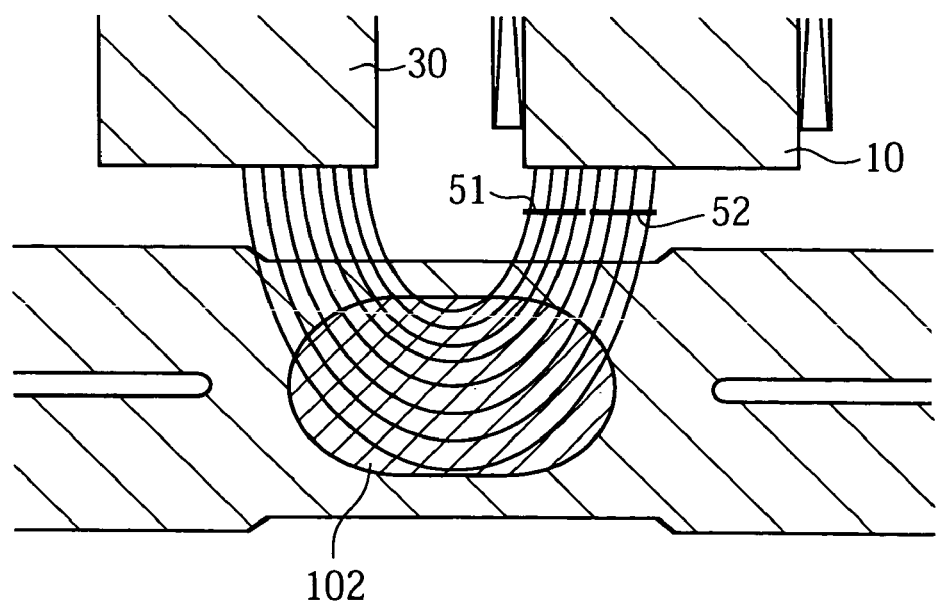
FIG. 20 shows one example of the cross-section of a spot weld section in a case where the detection results shown in FIG. 19 are obtained.
Figure 21:
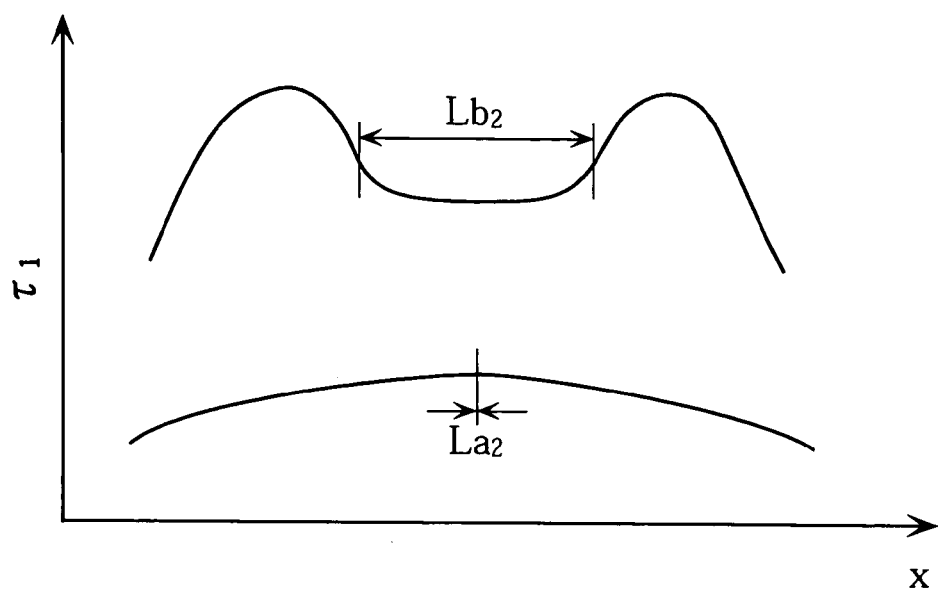
FIG. 21 shows a further example of detection results in a case where two coil rows of a non-destructive inspection device relating to the present invention are operated in a combined fashion.
Figure 22:
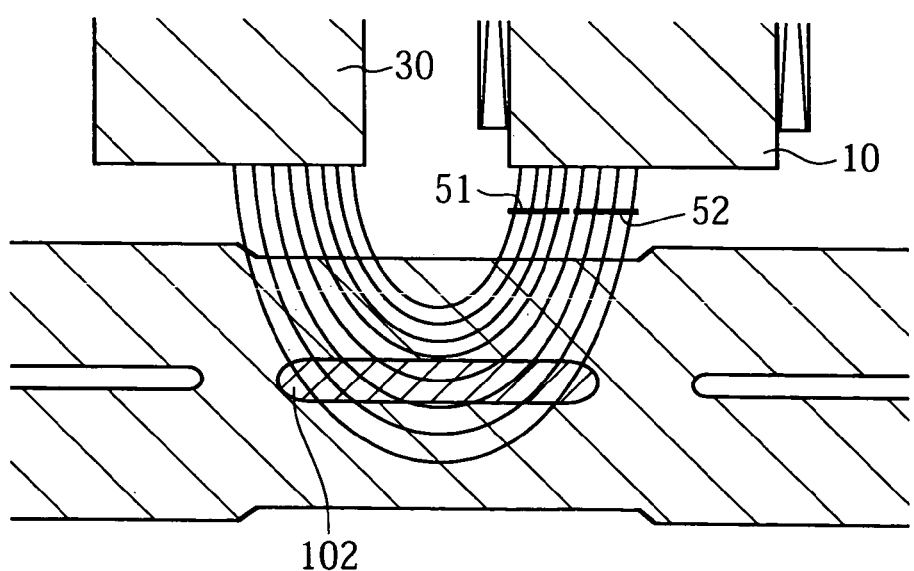
FIG. 22 shows one example of the cross-section of a spot weld section in a case where the detection results shown in FIG. 21 are obtained.
Figure 23:
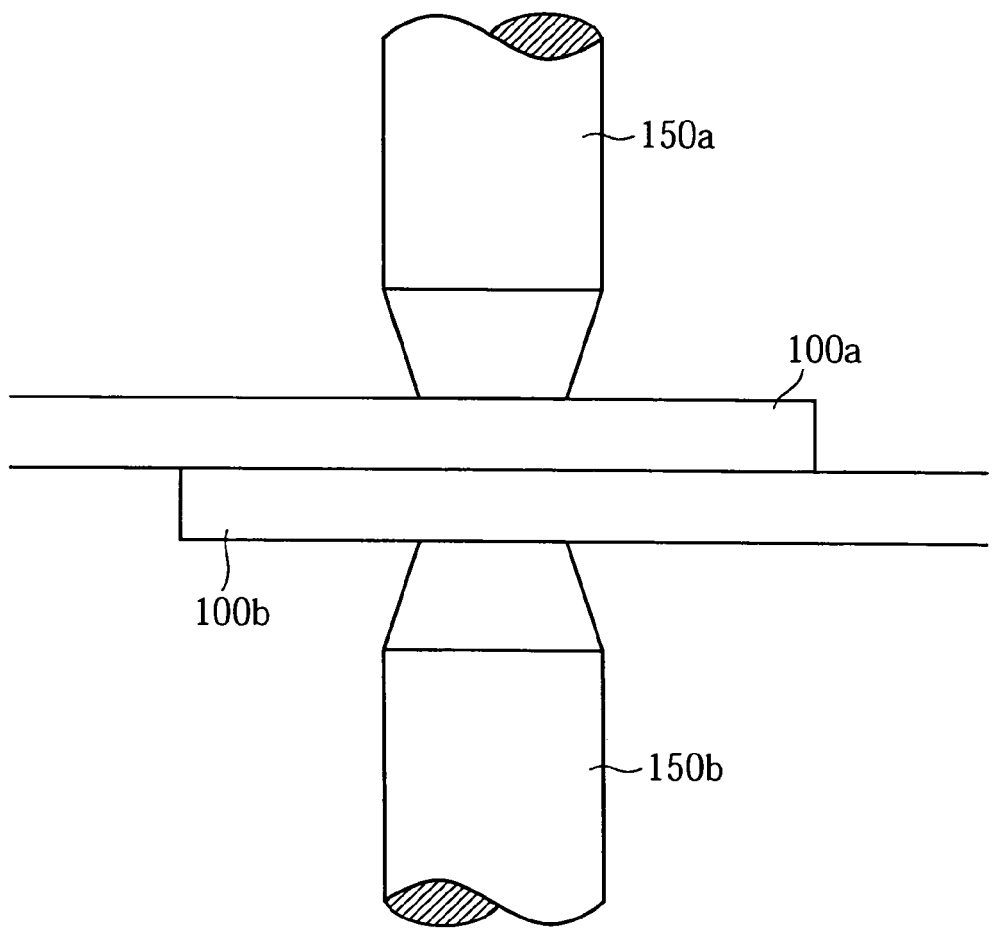
FIG. 23 is a diagram showing a spot weld.

FIG. 19 shows two analytical graphs (second-order differential curves of the approximation curves) obtained for a series of measurements of $\tau_1$ from the respective coil rows 51, 52, in a case where the nugget section 102 is thick in size, as illustrated in FIG. 20, for example. Graph G1 is obtained from the detection carried out using the first coil row 51, and graph G2 is obtained from the detection carried out using the second coil row 52. The dimension relating to the nugget section 102 inferred on the basis of the graph G1 is taken to be $La_1$ and the dimension relating to the nugget section 102 inferred on the basis of the graph G2 is taken to be $Lb_1$. FIG. 21, on the other hand, shows two analytical graphs (second-order differential curves of the approximation curves) obtained for a series of measurements of $\tau_1$ from the respective coil rows 51, 52, in a case where the nugget section 102 is thin in size, as illustrated in FIG. 22, for example. Graph G1' is obtained from the detection carried out using the first coil row 51, and graph G2' is obtained from the detection carried out using the second coil row 52. The dimension relating to the nugget section 102 inferred on the basis of the graph G1' is taken to be $La_2$ and the dimension relating to the nugget section 102 inferred on the basis of the graph G2' is taken to be $Lb_2$. If the nugget section 102 is thin, as in FIG. 22, then it may arise that the magnetic flux passing through a loop coil 51$a$ in the first coil row 51 hardly passes through the nugget section 102, and in such cases, the value of $La_2$ will be very small, or equal to zero, as shown in FIG. 21.

For example, focusing on the parameters $La_1/Lb_1$ and $La_2/Lb_2$, there are many cases where these values will differ according to the shape of the nugget section 102. Even in cases where the dimensional information $Lb_1$, $Lb_2$ obtained by detection using the second coil row 52 have mutually proximate values, if there is a significant difference between the values of the dimensional information $La_1$, $La_2$, then there will be a significant difference between the parameters $La_1/Lb_1$ and $La_2/Lb_2$. This difference will reflect information relating to the thickness of the nugget section 102.

In this way, by means of the non-destructive inspection device X1, it is possible to obtain a greater amount of information by carrying out inspection based on combined use of two coil rows 51, 52, and therefore, the nugget diameter L2, and the like, can be inferred to a greater degree of accuracy.

Above, the present invention was described by taking as examples a non-destructive inspection device and a non-destructive inspection method for a spot weld section. The present invention is not limited to this and may be applied to a device and method for measuring and inspecting internal defects, hardness, applied stress, and the like, in a magnetic member made of steel, or the like, in a non-destructive manner. Moreover, the visual concepts of the non-destructive inspection method were described by means of graphs, but it is also possible to process and analyze data in a variety of ways, by means of calculational processing based on functions corresponding to these respective graphs.

The invention claimed is:

1. A non-destructive inspection device comprising:
an exciting pole including a magnetic flux exciting surface for exciting a magnetic flux to form a magnetic field in an inspection target;
a recovering pole including a magnetic flux recovering surface for recovering the magnetic flux excited from the magnetic flux exciting surface; and
a coil ray including a plurality of loop coils though which the magnetic flux excited from the magnetic flux exciting surface passes prior to reaching the inspection target, the coil array facing the magnetic flux exciting surface,
wherein the magnetic flux exciting surface includes a first edge located closer to the recovering pole and a second edge located farther from the recovering pole than the first edge, and
wherein the coil array extends along the first and second edges and the plurality of loop coils are offset toward the recovering pole to be located closer to the first edge than to the second edge.

2. The non-destructive inspection device according to claim 1, wherein the plurality of loop coils are disposed within a region between a center of the magnetic flux exciting surface as viewed widthwise thereof and the first edge of the magnetic flux exciting surface.

3. The non-destructive inspection device according to claim 1, wherein a distance of separation between the magnetic flux exciting surface and the magnetic flux recovering surface is 1.0 to 2.0 mm.

4. The non-destructive inspection device according to claim 1, wherein the magnetic flux exciting surface and the magnetic flux recovering surface are congruent in shape.

5. The non-destructive inspection device according to claim 1, wherein the magnetic flux exciting surface is entirely equal in width to a trunk portion of the exciting pole.

6. The non-destructive inspection device according to claim 1, wherein the loop coils of the coil array constitute a plurality of coil rows, each coil row aligned parallel to the first and second edges.

7. A non-destructive inspection method carried out using a non-destructive inspection device comprising: an exciting pole including a magnetic flux exciting surface for exciting a magnetic flux to form a magnetic field in an inspection target; a recovering pole including a magnetic flux recovering surface for recovering the magnetic flux excited from the magnetic flux exciting surface; and a coil array including a plurality of loop coils though which the magnetic flux excited from the magnetic flux exciting surface passes prior to reaching the inspection target, the coil array facing the magnetic flux exciting surface; wherein the magnetic flux exciting surface includes a first edge located closer to the recovering pole and a second edge located farther from the recovering pole than the first edge; and wherein the coil array extends alone the first and second edges and the plurality of loop coils are offset toward the recovering pole to be located closer to the first edge than to the second edge; the method comprising:

a step of magnetizing the inspection target by applying a first static magnetic field to the inspection target;

a step of shutting off the first static magnetic field and measuring transient change in a differential magnetic flux density at a plurality of positions in a first residual magnetic field passing through the magnetized inspection target;

a step of determining a first time constant by a main time constant of the transient change at the respective measurement positions;

a step of magnetizing the inspection target by applying a second static magnetic field to the inspection target;

a step of shutting off the second static magnetic field and measuring the transient change of the differential magnetic flux density at the respective measurement positions in a second residual magnetic field passing through the magnetized inspection target;

a step of determining a second time constant by the main time constant of the transient change at the respective measurement positions; and an information acquisition step of obtaining information relating to the internal structure of the inspection target, on the basis of the differences between the distribution of the first time constant and the distribution of the second time constant, at the measurement positions.

8. The non-destructive inspection method according to claim 7, wherein the inspection target is a spot weld section in a joined member formed by spot welding of two metal plates, and information relating to the shape of the nugget section contained in the spot weld section, is obtained in the information acquisition step.

* * * * *